(12) United States Patent
Klopotek

(10) Patent No.: US 6,730,123 B1
(45) Date of Patent: May 4, 2004

(54) ADJUSTABLE INTRAOCULAR LENS

(75) Inventor: Peter J. Klopotek, Framingham, MA (US)

(73) Assignee: Proteus Vision, LLC, Wellesley, MA (US)

( * ) Notice: Subject to any disclaimer, the term of this patent is extended or adjusted under 35 U.S.C. 154(b) by 0 days.

(21) Appl. No.: 09/599,232

(22) Filed: Jun. 22, 2000

(51) Int. Cl.[7] ................................................. A61F 2/16
(52) U.S. Cl. ..................................................... 623/6.22
(58) Field of Search .............................. 623/6.13, 6.22, 623/6.31, 6.37; A61F 2/16

(56) References Cited

U.S. PATENT DOCUMENTS

| | | | |
|---|---|---|---|
| 3,598,479 A | 8/1971 | Wright | 351/159 |
| 3,677,667 A | 7/1972 | Morrison | 417/474 |
| 3,963,380 A | 6/1976 | Thomas, Jr. et al. | 417/322 |
| 4,298,996 A | 11/1981 | Barnet | 3/13 |
| 4,373,218 A * | 2/1983 | Schachar | 623/6.13 |
| 4,466,705 A | 8/1984 | Michelson | 350/418 |
| 4,564,267 A | 1/1986 | Nishimoto | 350/379 |
| 4,583,924 A | 4/1986 | Zenglein et al. | 417/420 |
| 4,585,457 A | 4/1986 | Kalb | 623/6 |
| 4,601,545 A | 7/1986 | Kern | 350/347 |
| 4,685,921 A | 8/1987 | Peyman | 623/6 |
| 4,685,922 A | 8/1987 | Peyman | 623/6 |
| 4,709,996 A | 12/1987 | Michelson | 350/418 |
| 4,790,847 A | 12/1988 | Woods | 623/6 |
| 4,816,031 A | 3/1989 | Pfoff | 623/6 |
| 4,842,601 A | 6/1989 | Smith | 623/6 |
| 4,913,536 A | 4/1990 | Barnea | 350/419 |
| 4,932,966 A | 6/1990 | Christie et al. | 623/6 |
| 4,950,289 A * | 8/1990 | Krasner | 623/6.13 |
| 4,994,082 A | 2/1991 | Richards et al. | 623/6 |
| 5,066,301 A | 11/1991 | Wiley | 623/6 |
| 5,108,429 A | 4/1992 | Wiley | 623/6 |
| 5,171,266 A | 12/1992 | Wiley et al. | 623/6 |
| 5,203,788 A | 4/1993 | Wiley | 623/6 |
| 5,275,623 A | 1/1994 | Sarfarazi | 623/6 |
| 5,443,506 A | 8/1995 | Garabet | 623/6 |
| 5,494,415 A | 2/1996 | Morita | 417/412 |
| 5,684,637 A * | 11/1997 | Floyd | 359/666 |
| RE36,150 E | 3/1999 | Gupta | 623/6 |
| 5,964,802 A * | 10/1999 | Anello et al. | 623/6.13 |
| 6,096,078 A * | 8/2000 | McDonald | 623/6.22 |
| 2003/0060878 A1 * | 3/2003 | Shadduck | 623/6.13 |

FOREIGN PATENT DOCUMENTS

| | | |
|---|---|---|
| GB | 2273133 | 2/1994 |
| SU | 1810052 | 4/1993 |
| WO | 9929266 | 6/1999 |

OTHER PUBLICATIONS

Stefan Kluge, et al—"Mikroelektronik liefert Grundlagen fur Mikropumpen," *Transfer* (15); 50–54 (1996).

* cited by examiner

*Primary Examiner*—David H. Willse
*Assistant Examiner*—Javier G. Blanco
(74) *Attorney, Agent, or Firm*—Thomas J. Engellenner; Reza Mollaaghababa; Nutter McClennen & Fish, LLP

(57) ABSTRACT

The present invention provides an intra-ocular lens (IOL) whose focusing performance can be modified after its implantation in the eye without a need for any invasive procedure. An IOL of the invention has an optical chamber having at least a flexible region that is deformable under influence of a fluid. The IOL further include a reservoir for storing an optical fluid in fluid communication with the optical chamber, and a valve that regulates the fluid communication between the reservoir and the optical chamber. The lens can also include a pump that is actuated by an external energy source to transfer the optical fluid between the reservoir and the optical chamber to change the amount of fluid in the optical chamber, thereby modifying the focusing performance of the IOL.

49 Claims, 23 Drawing Sheets

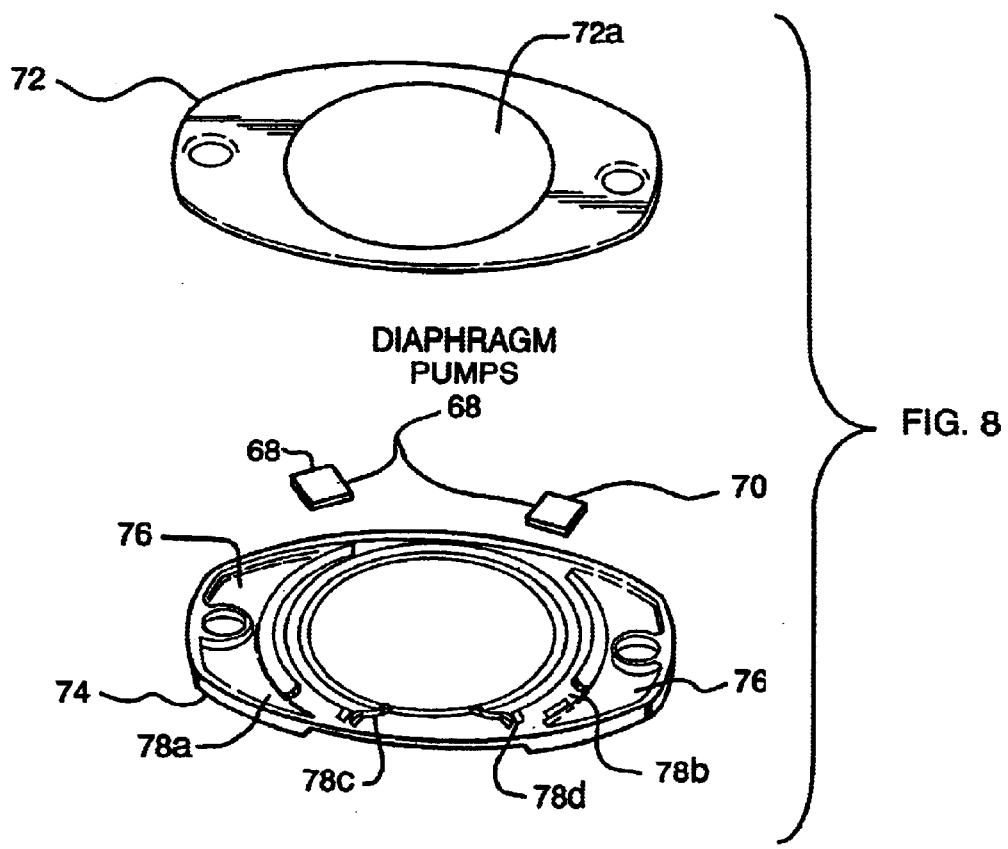

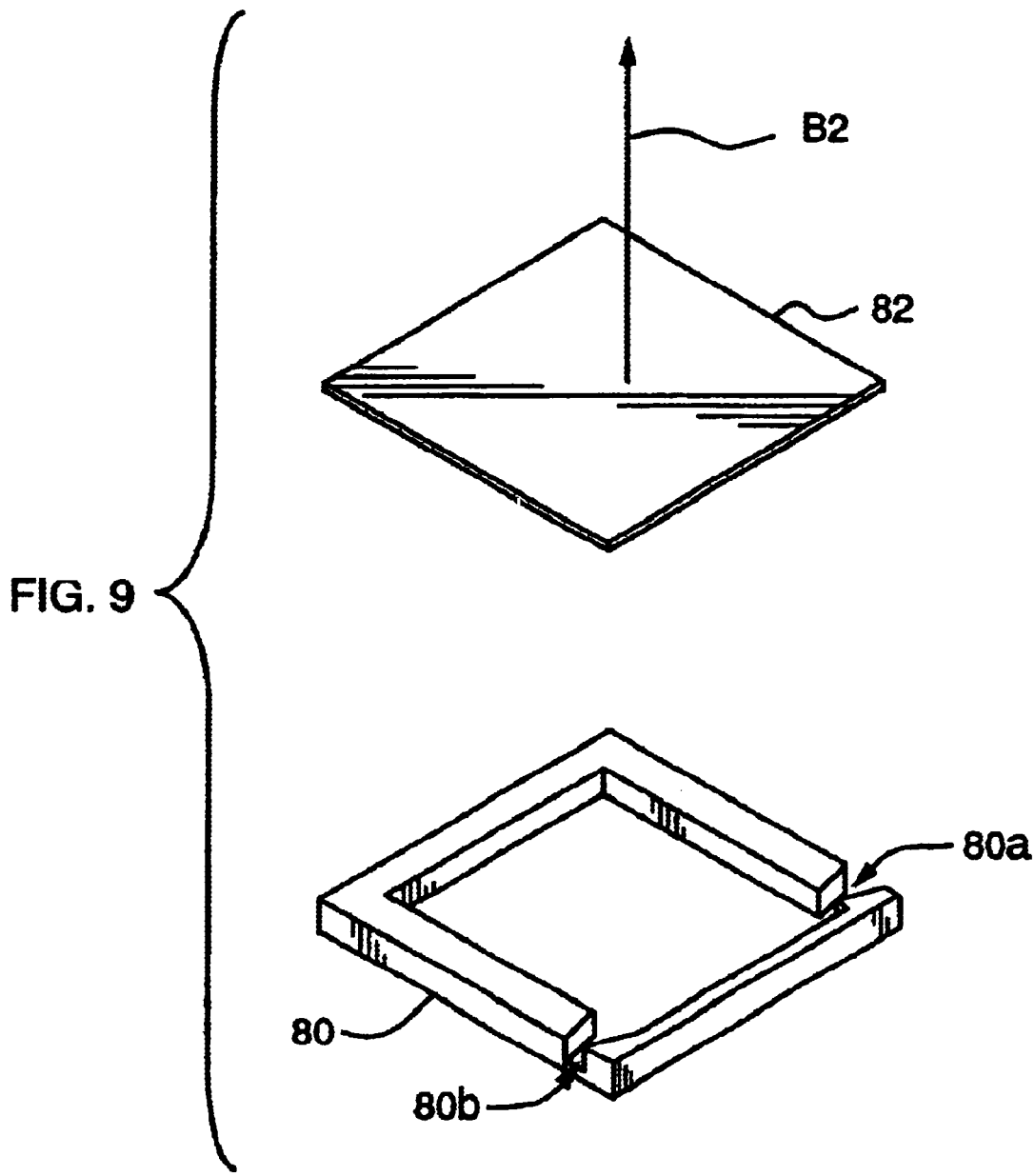

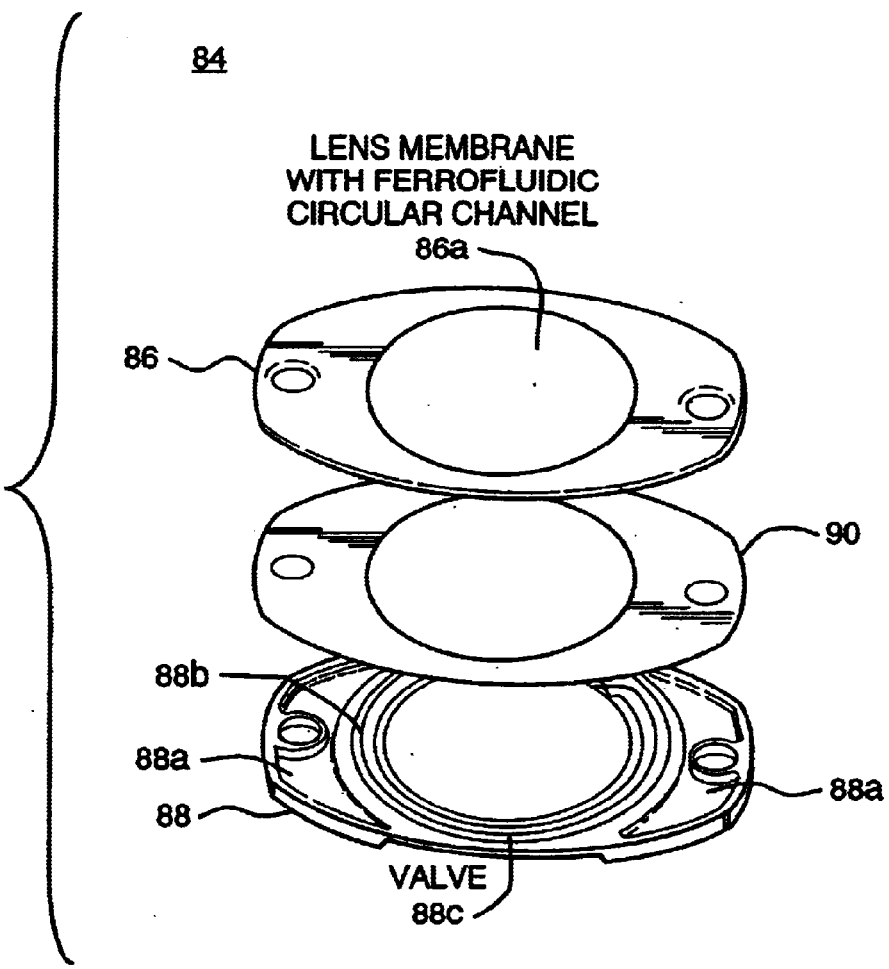

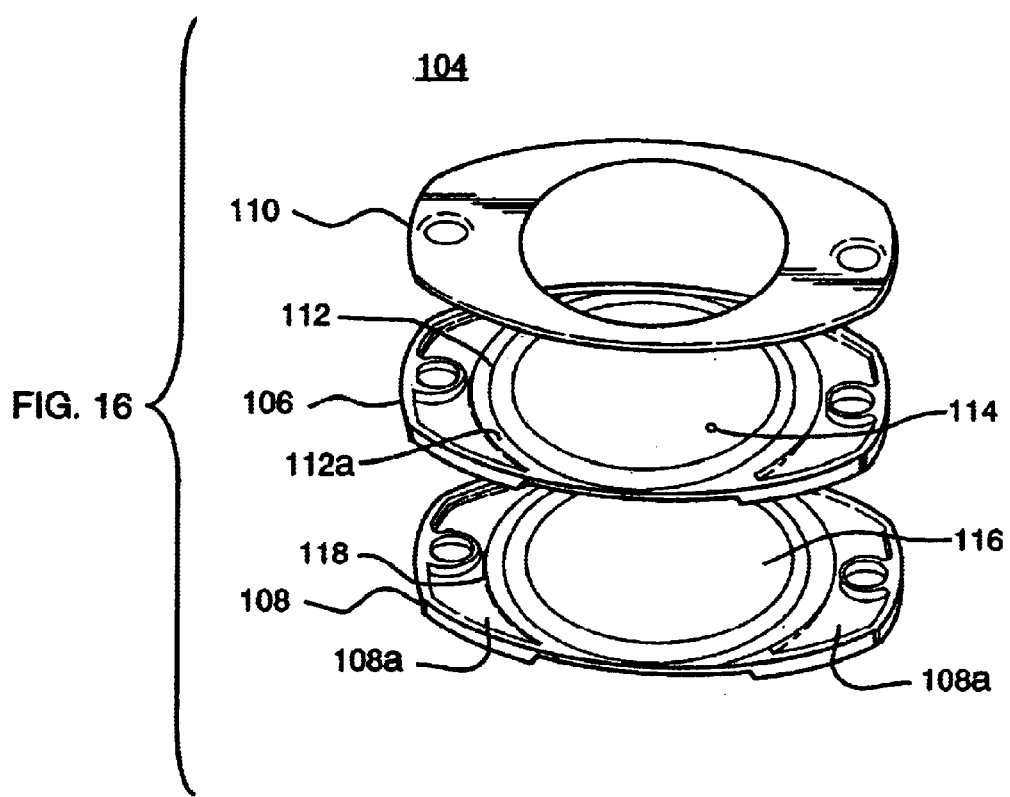

ADJUSTABLE INTRAOCULAR LENS

BACKGROUND OF THE INVENTION

The present invention relates generally to intraocular lenses, and more particularly to intraocular lenses whose focusing performance can be adjusted externally after implantation in an individual's eye, without a need for any invasive procedure.

The lens and the cornea of the human eye provide a combined refractive power of approximately 60 diopters (D), with the cornea providing about 40 D of the power and the lens providing about 20 D of the refractive power. Certain diseases of the eye, such as cataracts, cause the lens to become progressively opaque. The opacity typically worsens over time, and can ultimately result in blindness. It is typically necessary to surgically remove the opaque lens to allow an unobstructed transmission of light to the retina. The removal of the lens, however, deprives the eye from the substantial refractive power that the lens provides.

When the natural lens is removed from the eye, an intraocular lens (IOL) can be implanted in the eye to assist the eye in focusing light onto the retina. Intraocular lenses typically provide one or more fixed focusing performances. Typically, the needed refractive correction(s) is (are) determined before implantation of the IOL in the eye. Such pre-operative predictions of the needed corrective power are sometimes not sufficiently accurate. Furthermore, once implanted, an IOL can shift position within the eye, thereby causing a loss of focus. Hence, an individual having an implanted IOL may require additional corrective devices, such as glasses, to acquire the desired visual acuity.

Accordingly, it is object of the present invention to provide an intraocular lens whose focusing performance can be modified in situ.

It is another object of the invention to provide an intraocular lens whose focusing performance can be externally modified after implantation in the eye.

It is yet another object of the invention to provide an intraocular lens whose focusing performance can be adjusted over a selected range.

SUMMARY OF THE INVENTION

The present invention attains the above and other objects by providing an intraocular lens whose focusing performance can be adjusted over a selected range after implantation in a patient's eye without a need for an invasive procedure. In particular, the focusing performance of an IOL according to the invention can be modified by application of energy, such as magnetic or electric energy, supplied from an external source to the IOL. An intraocular lens according to the teachings of the invention includes an optical chamber deformable under influence of pressure from a fluid. The IOL further includes a reservoir, in fluid communication with the optical chamber, for storing an optical fluid. A valve regulates the fluid communication between the reservoir and the optical chamber.

As used herein, the term "optic" or "optical body" is intended to encompass the component(s) within the intraocular lens of the present invention that cumulatively enable the intraocular lens to focus the light. The optic can include an optical chamber and optical fluid within such chamber, as well as one or more physical lens structures, if desired. The term "intraocular lens", as used herein, encompasses all of the above described optical elements and other structures such as haptics useful for attaching the IOL to the eye as well as other structures elaborated below.

The IOL can further include a pump capable of being actuated by an energy source external to the eye to cause a flow of a selected volume of the optical fluid between the reservoir and the optical chamber. A flow of the optical fluid into and/or out of the optical chamber selectively varies an amount of fluid in the optical chamber. The change in the amount of fluid in optical chamber can vary a pressure exerted on the flexible portion(s) of the optical chamber to cause a change in radius of curvature of the flexible portion (s) and/or vary a distance between optical surfaces of the optical chamber. Such changes in the optical chamber can lead to a change in the focusing performance of the IOL.

The external energy source can include, but is not limited to, a magnetic field generator, an electric field generator, or a source of photons, such as a laser. In one preferred embodiment, an oscillatory magnetic field is employed for actuating the pump. In another embodiment, a rotating magnetic field is employed for activating the pump.

In general, the index of refraction of the optical fluid useful in the present invention can have any value. In most implementations, however, the index of refraction of the optical fluid is preferably selected to be greater than approximately 1.337. One preferred embodiment of the invention employs silicone with an index of refraction of about 1.4 as the optical fluid.

In many implementations, the IOL can include an optical body having two optical elements, at least one of which has a flexible convex region. These elements form an optical chamber therebetween. In such an embodiment, pumping a volume of the optical fluid into the chamber increases the hydrostatic pressure within the optical chamber and hence causes a decrease in the radius of curvature of the flexible region of the chamber. Such a decrease in the radius of curvature, in combination with the focusing performance of the fluid, leads to an increase in the focusing performance of the intraocular lens.

The IOL device can also include one or more haptics to allow fixation of the lens within the eye. The haptics can also include the reservoir of fluid for use in modifying the shape of the optical chamber.

One embodiment of the present invention provides an intraocular lens that employs a gear-pump. Such an intraocular lens includes an optical body having at least an optical chamber with at least a flexible region deformable in response to an applied pressure. A reservoir, which is in fluid communication with the optical chamber through a valve positioned between the reservoir and the optical chamber, stores a selected volume of an optical fluid. The gear pump is configured to be actuated by an energy source positioned external to the eye to cause the optical fluid to move, through the valve, between the optical chamber and the reservoir.

The gear pump can include a pair of inter-locking gears formed, for example, of silicone rubber. At least one of the gears is selected to be magnetically rotatable, for example, by implanting a permanent magnet in the silicone rubber. An external magnetic field generator can be utilized to apply a rotating magnetic field to the magnetic gear to cause a rotation thereof. The rotation of the magnetic gear in turn causes a rotation of the other gear, i.e., the gear engaged with the magnetic gear, in an opposed direction. The combined rotation of the gears controls the flow of the optical fluid between the reservoir and the optical chamber of the lens.

Another preferred embodiment of the invention employs a peristaltic pump for providing fluid communication between an optical chamber and a reservoir of an optical fluid. The peristaltic pump can also include a valve for regulating the flow of the optical fluid between the reservoir and the optical chamber. A magnetic field, such as an external rotating magnetic field, actuates the peristaltic pump according to the invention by inducing a propagating deformation, e.g., constriction, therein, which causes a flow of the optical fluid between the reservoir and the optical chamber. Thus, by actuating the pump, the clinician (or the subject) can calibrate or tune the focusing performance of the IOL to a desired value.

A peristaltic pump according to the teachings of the invention can have a tubular structure that is formed, for example, of a resilient material such as silicone rubber, or another polymeric elastomer. A plurality of magnetic particles, such as ferrite, magnetite, nickel cobalt, neodymium, boron, samarium, iron or compounds or alloys of such materials, are distributed within the wall of the tubular structure such that a rotating magnetic field can be applied to the tubular structure to induce a propagating constriction within the tubular structure. The propagating constriction causes the optical fluid within the tubular structure to flow from one end of the structure to the other, thereby inducing the fluid flow between the reservoir and the optical chamber.

Another embodiment of an intraocular lens according to the teachings of the present invention utilizes a diaphragm pump to transfer an optical fluid between an optical chamber, formed in the optical body, and a reservoir for storing the optical fluid. The diaphragm pump can be actuated by an energy source positioned external to the eye. For example, the diaphragm pump can be magnetically and/or electrically actuated.

The diaphragm pump can include a housing having an inlet opening and outlet opening, and further can include a flexible diaphragm disposed in mechanical communication with the housing. The diaphragm can be formed of a material such as Silicon (Si), Titanium, Stainless Steel, and can be selected to have at least one resonant vibrational frequency. Alternatively, the diaphragm can be formed of elastomeric materials such as poly(dimethylsiloxane) (PDMS). Application of an oscillatory magnetic field having an oscillation frequency which is substantially similar to the resonant vibrational frequency of the diaphragm induces a large amplitude oscillation in the diaphragm, and thereby causes a flow of the fluid between the inlet and the outlet openings.

In yet another embodiment of the invention, the intraocular lens can employ a peristaltic micro-pump utilizing a ferro-fluid material. The IOL can again include an optical body having a base portion and a cover portion that form an optical chamber therebetween. At least one of the cover or the base portions has a flexible region that is deformable in response to an applied pressure. The base portion includes a reservoir for storing an optical fluid, and further has a channel for providing fluid communication between the reservoir and the optical chamber by providing a flow path for the optical fluid. The cover portion has a channel for storing a ferro-fluid material. The channels of the base portion and the cover portion are preferably substantially aligned. A flexible membrane disposed between the channels of the base and the cover portions isolates the ferro-fluid from the optical fluid. The ferro-fluid material can be externally actuated, for example by an external magnetic energy source, to provide a propagating pressure on the flexible membrane. The propagating pressure in turn produces a propagating deformation of the membrane to cause transfer of a selected volume of the optical fluid between the reservoir and the optical chamber. Ferro-fluid materials suitable for use in the intraocular lens of the invention can include oil-based ferrofluids such as silicone oil or petroleum distillate suspension of nanoparticles of magnetite ($Fe_3O_4$), Iron, Cobalt, Iron nitride ($Fe_3N$) in which the nanoparticles are typically coated with an ultra-thin layer of surfactant to keep the particles suspended.

In another aspect, the invention provides an intraocular lens that has an optical body having at least an optical chamber and at least a flexible region that is deformable under influence of a fluid. Further, the IOL includes a reservoir for storing a selected volume of an optical fluid. The reservoir is in fluid communication with the optical chamber through a valve which regulates the flow of the optical fluid between the reservoir and the optical chamber. The IOL includes at least one magnet positioned between the reservoir and the optical chamber and pivoted about a rotation axis at an end thereof. A magnetic field supplied by an external magnetic energy source can actuate the magnet to cause it to rotate about its pivot point, thereby forcing the flow of the fluid in a selected direction, for example, from the reservoir to the optical chamber. The IOL can also include a second magnet positioned along a vector directed from one pole of the first magnet to its other pole such that the opposite poles of the first and second magnets are proximate of each other. The magnets can be actuated by an external magnetic source to rotate in opposite directions, albeit about the same rotational axis, to cause a flow of the optical fluid through the valve between the reservoir and the optical chamber.

Another intraocular lens according to the teachings of the invention employs a micro-pump that utilizes at least one ball formed of a magnetic material. Such magnetic material is preferably selected to be soft and can include, for example, silicon steel alloys (2.5%–6% Si and Fe in balance) or iron-cobalt alloys such as, Fe—Co—V—Nb alloys, e.g., Carpenter Hiperco alloy. Such an IOL includes an optical body having a base portion and a cover portion that form an optical chamber therebetween. The base portion has at least a flexible region and further has a reservoir which is in fluid communication with the optical chamber. Further, the cover portion has a channel that includes a surface having at least a flexible portion in contact with at least a portion of the fluid. A valve positioned between the reservoir and the optical chamber regulates the fluid communication between the reservoir and the optical chamber. The ball is positioned in the channel of the cover portion and is actuated by an external magnetic source to move within the channel such that it produces a deformation of the flexible membrane. This deformation, produced in the vicinity of the ball, in turn causes a flow of the fluid through the channel between the reservoir and the optical chamber.

Although the invention is described in terms of discrete "base" and "cover" portions, it should be clear that an IOL of the invention can be constructed as a unitary structure having two surfaces corresponding to the base and cover portions described above. Moreover, even when two components are formed in manufacturing of the IOL, the construction process can be such that the "base" and "cover" components are completely fused so as to form an essentially unitary structure.

A further embodiment of an IOL of the invention can employ the Faraday effect to actuate a piezo-electric element which in turn actuates a diaphragm pump. In particular, the IOL includes an optical body having an optical chamber and at least a flexible region that is deformable in response to an applied pressure. The optical body further includes a reservoir for storing an optical fluid. The piezo-electric element can be actuated by energy, such as a time-varying magnetic flux, provided by an external source, to cause the diaphragm pump to transfer a selected volume of the optical fluid between the reservoir and the optical chamber.

The piezo-electrically driven diaphragm pump can include a housing having inlet and outlet openings (which can be one-way valves), a flexible membrane that is in mechanical communication with the housing, and a piezo-electric element in contact with the diaphragm. A periodic modulation of the stress in the piezo-electric element, induced, for example, by an oscillatory flux, can result in a mechanical oscillation of the diaphragm. Such an oscillation of the diaphragm forces a fluid within the diaphragm housing to flow between the inlet and the outlet openings of the diaphragm pump.

An intraocular lens according to another aspect of the invention can include a vapor-operated pump. The vapor-operated pump can include housing having a reservoir of a selected volume of a fluid, e.g., water, in contact with a flexible membrane. A resistive element, such as a resistor, energized by an external energy source can be employed to periodically turn the fluid into vapor, thereby providing a periodic pressure change against the flexible membrane. This periodic pressure change in turn causes a periodic deflection of the diaphragm that provides a pumping action for transferring fluid through the housing of the pump between an input port and an output port (which can be one-way valves).

In another aspect of the invention, a pump for transferring the optical fluid between the reservoir and the optical chamber employs reverse electrophoresis.

Illustrative embodiments of the invention will be described below with reference to the following drawings.

BRIEF DESCRIPTION OF THE DRAWINGS

FIG. 8 is an exploded perspective view of another embodiment of an IOL according to the teachings of the invention which employs a pair of diaphragm pumps, FIG. 9 is an exploded perspective view of a diaphragm pump that can be utilized in the embodiment of FIG. 8, FIG. 10 is an exploded perspective view of another embodiment of an IOL according to the teachings of the invention having a ferro-fluid pump.

FIG. 16 is an exploded perspective view of an IOL according to another embodiment of the invention which employs a magnetic ball for forcing an optical fluid to flow between a reservoir and an optical chamber.

DETAILED DESCRIPTION

The present invention provides an IOL whose focusing performance can be modified within a pre-defined range after it has been implanted in the eye of a patient, without any need for an invasive procedure. More particularly, the focusing performance of an IOL according to the teachings of the invention can be modified by employing an external energy source, such as a source providing an electric or a magnetic field, to provide an optical power that maximizes the visual acuity of the eye in which the IOL is implanted. An IOL according to the invention allows an external modification of its optical power within a selected range. One significant advantage of an IOL of the invention is that such a modification of its optical power can be accomplished without a need for an invasive procedure. That is, the focusing performance of an IOL of the invention can be modified by utilizing an energy source external/remote of the eye. A number of preferred embodiments of the invention will be described below. Those skilled in the art will appreciate that a number of modifications can be made to these embodiments without departing from the scope of the invention.

Figure 1A:
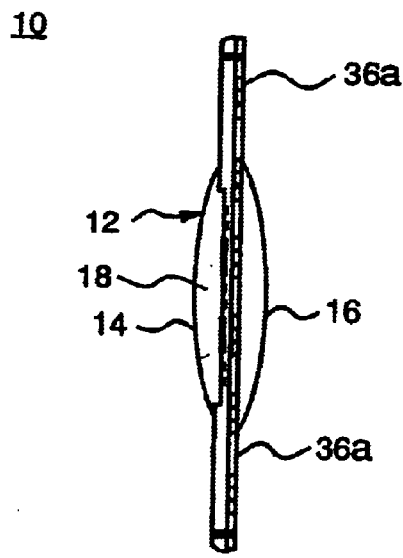
FIG. 1A is a schematic side view of an intraocular lens according to the teachings of the invention.
Figure 1B:
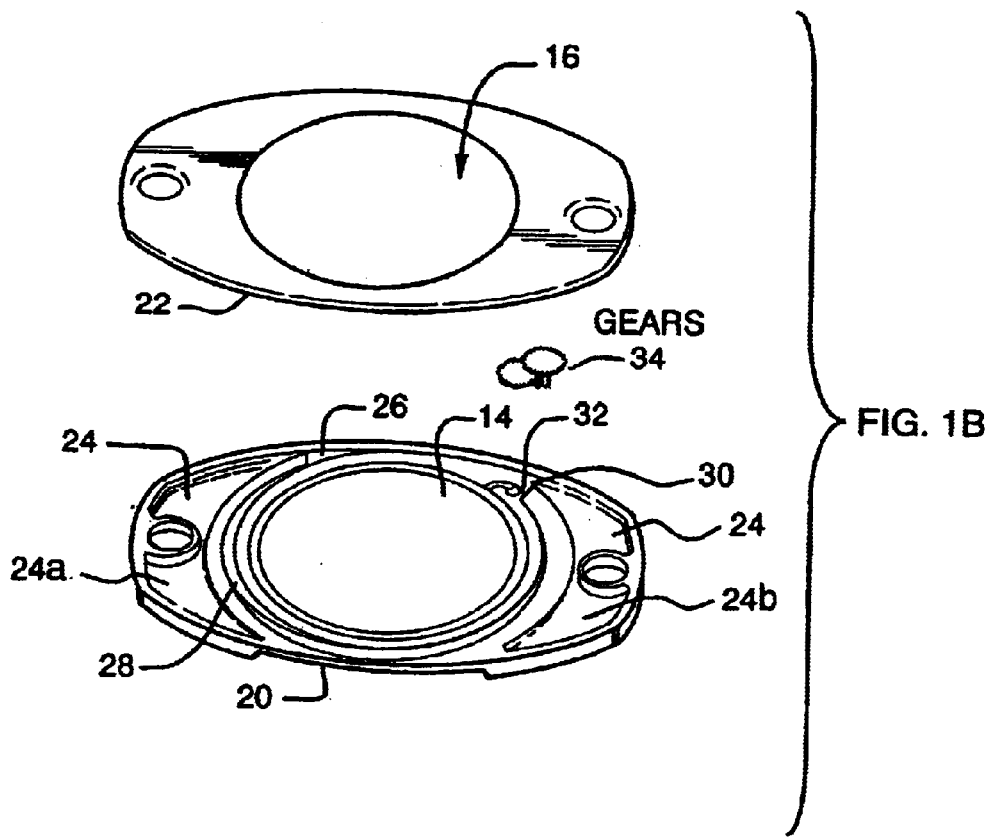
FIG. 1B is an exploded perspective view of the IOL of FIG. 1A.

FIGS. 1A and 1B illustrate an intraocular lens 10 according to one preferred embodiment of the invention that includes an optical body 12. The illustrated optical body 12 includes a membrane 16 and a membrane or an integral lens 14, at least one of which is deformable in response to an applied pressure. The membrane 16 and the membrane/integral lens 14 form an optical chamber 18 therebetween. An exploded perspective view of the IOL 10, shown in FIG. 1B, illustrates that the IOL 10 includes a base portion 20 having the membrane/integral lens 14 therein and a cover portion 22 having the membrane 16. The base portion 20 further includes a reservoir 24 having two portions 24a and 24b, in which an optical fluid (not shown), such as silicone, can be stored. A channel 26 provides fluid communication between the portions 24a and 24b of the reservoir 24, and another channel 28 provides fluid communication between the reservoir 24 and the optical chamber 18. A valve 30 regulates the fluid communication between the reservoir 24 and the optical chamber 18 in a manner described below.

The terms "base portion" and "cover portion", as used herein, are intended to encompass both discrete elements and surfaces of a unitary structure.

The housing portion 20 further includes a seat 32 for accommodating a pair of interlocking gears 34a,b which can be actuated by an external magnetic energy source to pump the optical fluid between the reservoir 24 and the optical chamber 18.

Figure 2:
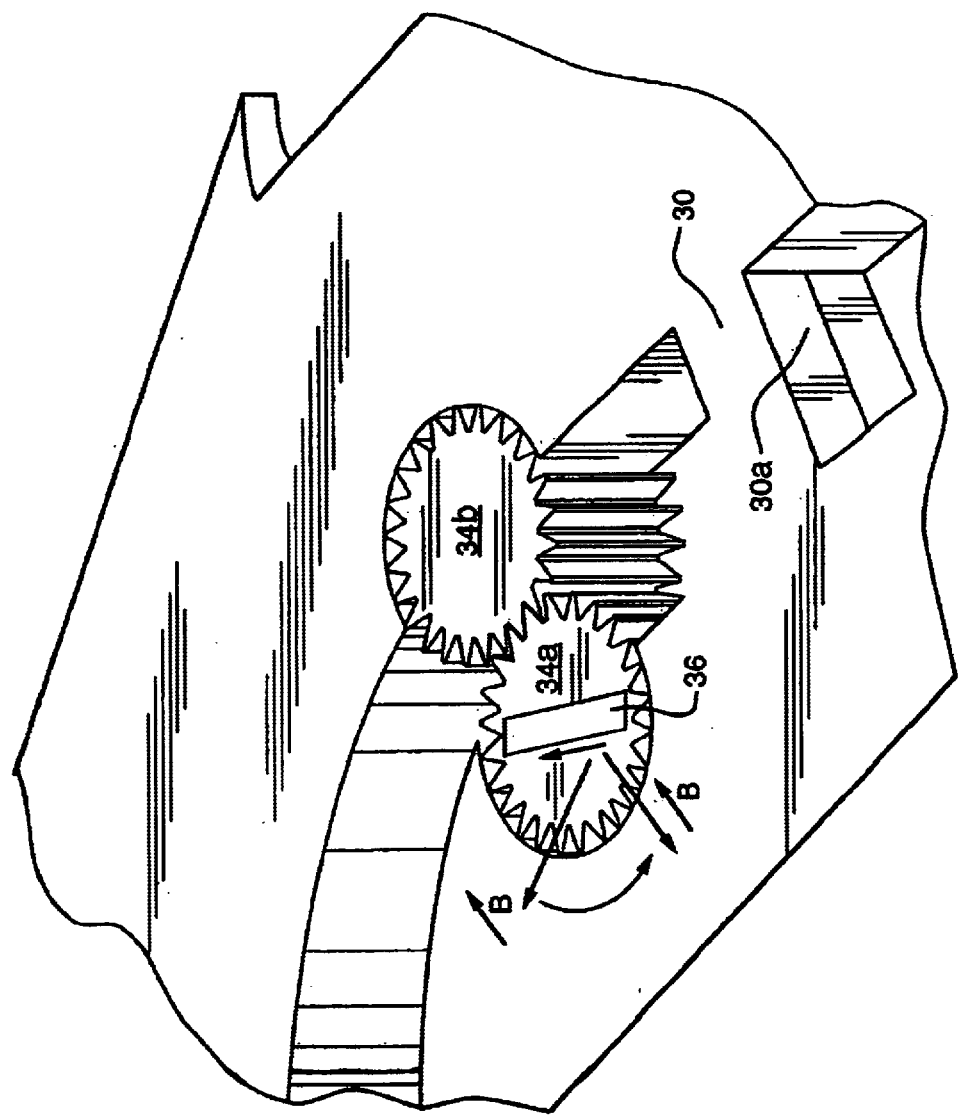
FIG. 2 is a fragmentary perspective view of the IOL of FIGS. 1A, 1B illustrating a gear pump, an embedded permanent magnet, and a valve according to the invention.

In one preferred embodiment of the invention, the base portion 20, the cover portion 22, and the gears 34a,b are formed of silicone rubber. Further, as shown in FIG. 2, a permanent magnet 36, embedded in the gear 34a, is selected to have a high internal magnetization. For example, the permanent magnet 36 can have Nd—Fe—B or Sm—Co—Fe compositions known in the art. The IOL 10 can be formed by utilizing any suitable manufacturing technique, such as injection molding.

The material for forming the membrane 16 and the membrane/lens 14 can be preferably selected such that its index of refraction is substantially similar to the index of refraction of the optical fluid utilized for modifying the focusing performance of the intraocular lens. For example, the membranes can be formed of silicone rubber when silicone is utilized as the optical fluid. The substantial similarity of the index of refraction of silicone rubber with that of silicone advantageously minimizes refraction of light at the boundaries between the membranes 14 and 16 and the liquid-filled optical chamber 18, thereby rendering the quality requirements of inner surfaces of the optical chamber 18 less stringent and/or minimizing optical abnormalities.

The IOL 10 further includes haptics 36a that are commonly used by practitioners to facilitate fixation of the IOL 10 in the eye.

Although the membrane 16 and the membrane/lens 14 in this illustrative embodiment are shown as convex, those skilled in the art will understand that the shapes of the membranes 14 and/or 16 can be selected such that the optical chamber is planoconvex so long as at least a portion of at least one of the membranes is sufficiently flexible to deform in response to an applied pressure. Further, one or both surfaces 14 and 16 can include a diffractive pattern, e.g., a Fresnel diffractive pattern, to enhance the focusing performance of the IOL and/or to compensate a chromatic aberration of the entire optical system including the IOL of the invention and the cornea.

FIG. 2 illustrates the positioning of the gears 34a and 34b in the seat 32. The gears 34a and 34b can include a core gear coated with a durable and slippery material. Some materials suitable for forming the core gear include, but are not limited to, titanium, diamond, $TiB_2$ and molybdenum disulfide. Such a construction of the gears 34a and 34b advantageously combines the strength of the core material with the slipperiness and durability of the coating. The gear 34a includes the permanent magnet 36 having a magnetic dipole moment that is schematically depicted by a vector m. An external magnetic field can be applied to the magnetic moment m of the gear 34a to cause its rotation, either clockwise or counterclockwise. A rotation of the gear 34a in turn causes a rotation of the interlocked gear 34b in an opposed direction, thereby forcing a flow of the optical fluid between the reservoir 24 and the optical chamber 18 (FIGS. 1A, 1B), i.e., either from the reservoir 24 to the optical chamber 18 or from the optical chamber 18 to the reservoir 24. Thus, the interlocking gears 34a and 34b form a gear pump that allows pumping optical fluid into or out of the inner chamber 18, to change the hydrostatic pressure applied to the flexible membranes 16 and/or the flexible membrane/lens 14, thereby modifying the refractive power of the IOL 10.

For example, the application of an exemplary external magnetic field B, which lies in a plane parallel to the upper surface of the gear 34a, to the gear 34a results in the application of a torque to this gear which in turn causes its rotation. In this illustrative example, the external magnetic field B causes a counter-clockwise rotation of the gear 34a, which in turn causes a clockwise rotation of the interlocking gear 34b. If the external magnetic field B is stationary, the rotation of the gear 34a ceases when the magnetic moment m and the external magnetic field B are aligned.

A rotating external magnetic field can be applied to the gear 34a to cause a continuous rotation thereof so long as the rotating magnetic field is present. For example, the illustrated external magnetic field B can be rotated in the plane in which it resides, to cause a continuous rotation of the gear 34a which in turn causes a rotation of the gear 34b in an opposite direction, thereby producing a pumping action for transferring the optical fluid between the reservoir 24 and the optical chamber 18 (FIGS. 1A, 1B).

In use, the gear pump 34 can be actuated by an external magnetic field supplied from an external energy source, to transfer an optical fluid between the reservoir 24 and the optical chamber 18. Energy sources for providing either a stationary or a rotating magnetic field are known in the art. Rotating magnetic fields can be found, for example, in widely used 3-phase electrical motors. Many stepper motors also employ rotating fields, where the rotation of the field is not continuous but is performed in many small steps. Further, devices that provide magnetic fields having oscillatory intensities are known. Such devices are typically made of inductors, e.g., coils, driven by oscillating currents.

Figure 3:
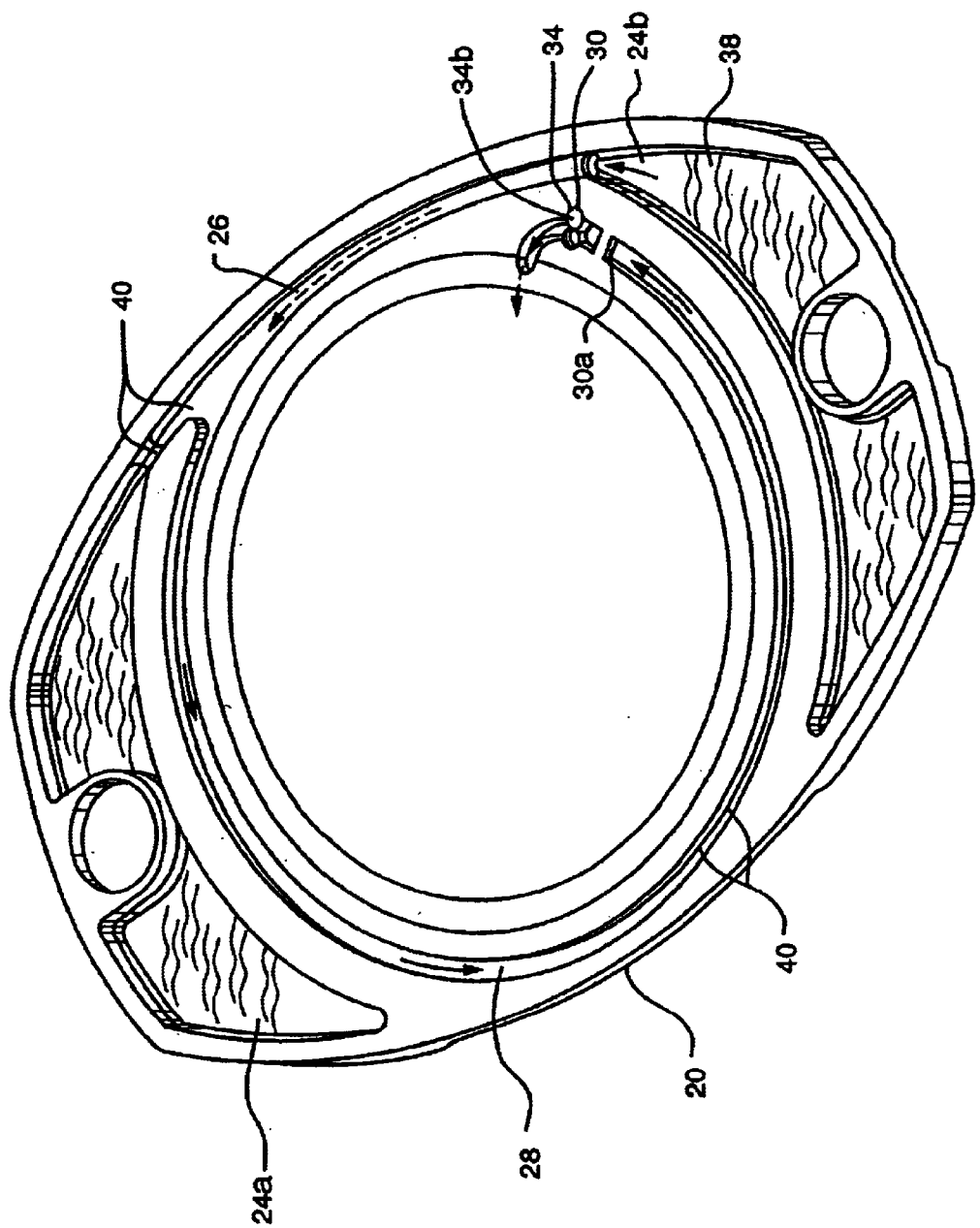
FIG. 3 is a perspective view of the base portion of the IOL of FIGS. 1A, 1B and 2.

FIG. 3 schematically illustrates an exemplary operation of the gear pump 34a,b. The reservoir 24 stores a selected volume of an optical fluid 38, such as silicone. After the IOL 10 is implanted in a patient's eye, there may be a need to increase its focusing performance. In such a case, an external rotating magnetic field can be applied to the gear pump 34, for example in a manner described above, to pump a selected volume of the optical fluid 38 from the reservoir 24 to the optical chamber 18 (FIG. 1A). A plurality of arrows 40 schematically illustrate the path of the optical fluid 38 flowing from the portions 24a and 24b to the optical chamber 18 (FIGS. 1A and 1B) under the pumping action of the gear pump 34. In particular, the gear pump 34 causes a flow of the fluid from the portions 24a and 24b of the reservoir 24 into the channel 28, and through the valve 30 into the optical chamber 18 (FIG. 1A). The valve 30 is preferably in the form of a slit 30a that provides an opening for the flow of the fluid when a pressure differential across it, produced by the gear pump 34, exceeds a selected threshold. The slit 30a can be formed, for example, by employing a diamond scalpel to slice a slit in a molded fluid barrier that can be made, for example, from a monolithic resin. Such micro slices advantageously provide a good match of the valve closing surfaces, thereby inhibiting leakage of fluid through the valve in the absence of a pumping action.

Those skilled in the art will appreciate that, in addition to slit valves, many other types of valves can be utilized for regulating the flow of the optical fluid in an IOL of the invention. Such valves can include, but are not limited to, flap valves, ball valves, nozzle valves, spring biased valves and gate structures.

An increase in the volume of the optical fluid within the optical chamber 18 (FIG. 1A) causes an increase of the hydrostatic pressure exerted against the membrane 16 and the membrane/lens 14. At least a portion of at least one of the membranes 14 and 16 is selected to be flexible. Hence, the increased hydrodystatic pressure renders the membranes more convex, i.e., it decreases the radius of curvature of each membrane, thereby increasing the optical power of the IOL 10. Those skilled in the art will appreciate that an IOL according to the teachings of the invention can function properly with only one flexible membrane. That is, it is sufficient that only one of the membrane 16 or the membrane/lens 14 be flexible to modify the optical power of the IOL 10 according to the teachings of the invention. Further, it is not necessary that the entire membrane be flexible. It is sufficient that a region of the membrane, for example the optical region, be sufficiently flexible to respond effectively to the hydrostatic pressure exerted thereon by the optical fluid in the optical chamber 18.

Alternatively, the gear pump 34 can be actuated to transfer a selected volume of the optical fluid from the optical chamber 18 to the reservoir 24 to lower the optical power of the IOL 18. For example, reversing the rotational direction of the external rotating magnetic field B, shown schematically in FIG. 2, can cause the rotation of the gear 34a in an opposite direction, thereby causing a flow of the fluid from the optical chamber to the reservoir 24.

Figure 4:
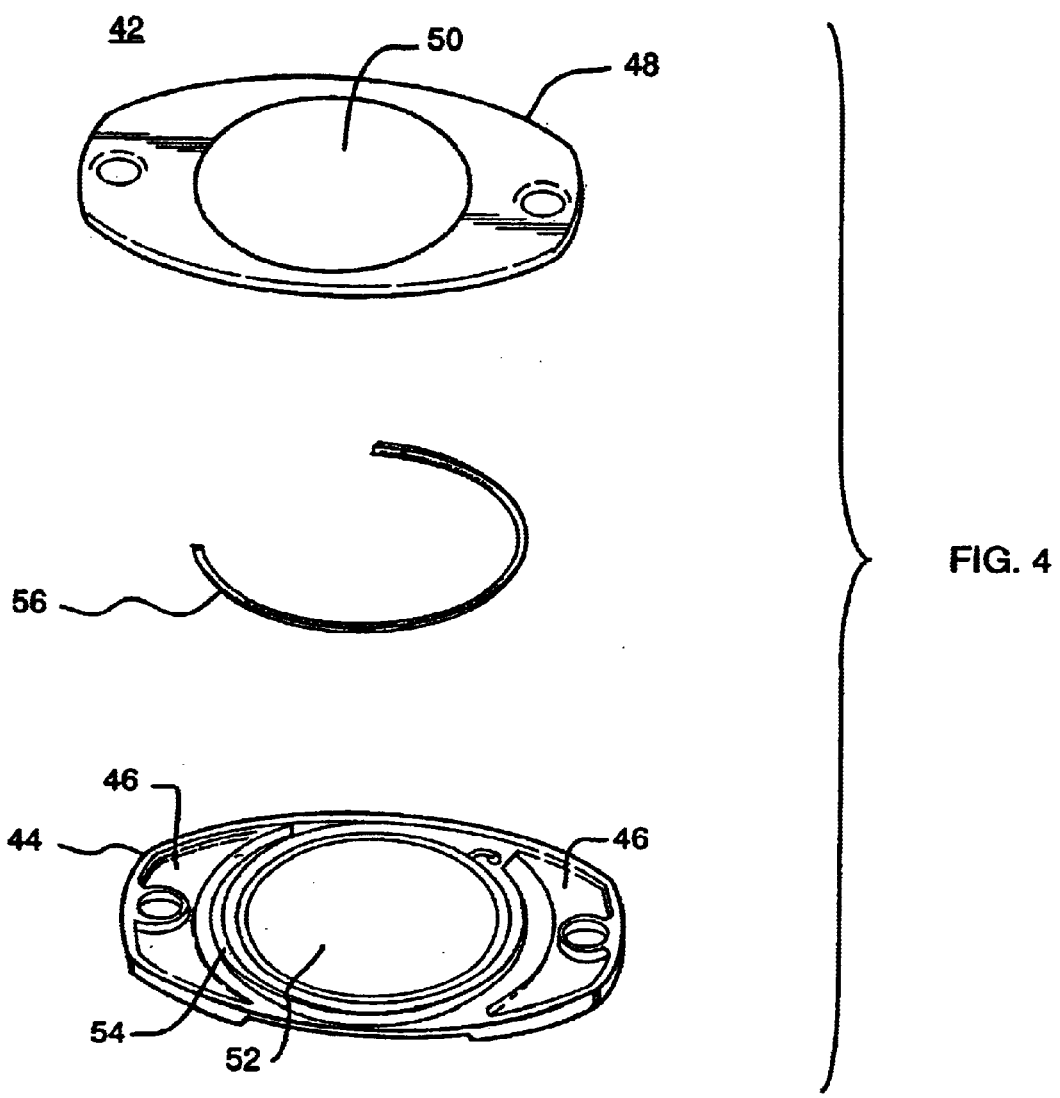
FIG. 4 is an exploded perspective view of an intraocular lens according to the teachings of the invention which employs a peristaltic pump.

FIG. 4 illustrates an exploded view of an intraocular lens 42 according to an alternative embodiment of the present invention. Similar to the IOL 10 of the previous embodiment, the IOL 42 includes a base portion 44 having a reservoir 46, and a cover portion 48. The illustrative cover portion 48 includes a flexible convex membrane 50 formed of an optical material. In addition, the base portion 44 includes a flexible membrane and/or integral lens 52, also formed of an optical material. A chamber, similar to the chamber 18 of FIGS. 1A,B, is formed between the membrane 50 and the membrane/lens 52. A channel 54 provides a seat for a peristaltic pump 56 which provides a pumping action for transferring an optical fluid (not shown), stored in the reservoir 46, between the reservoir 46 and the optical chamber.

Figure 5:
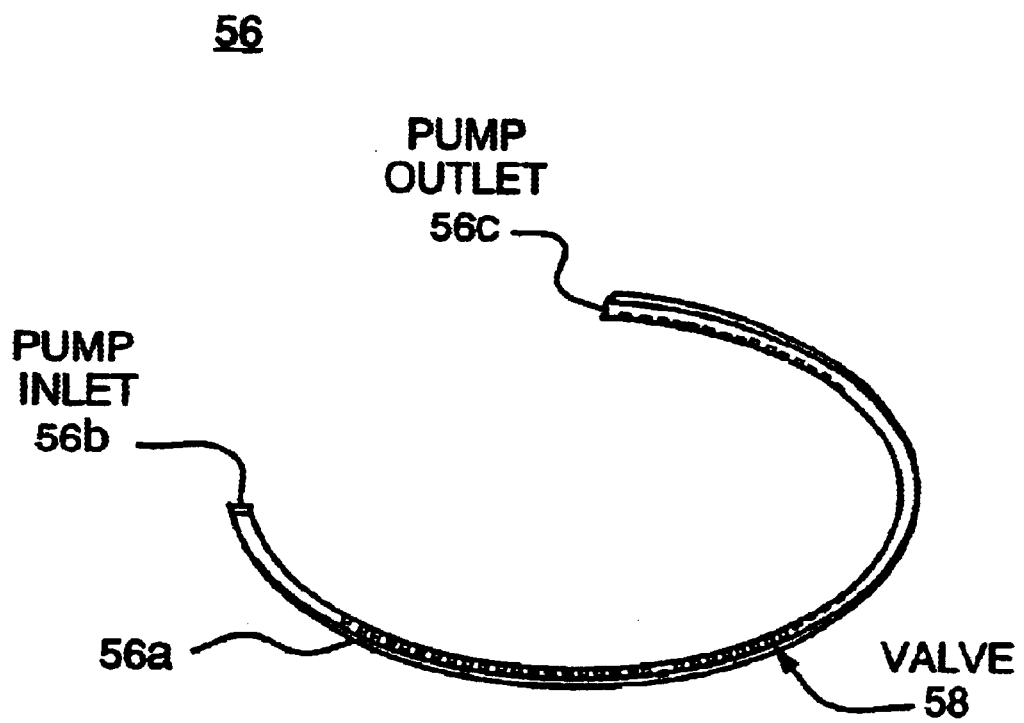
FIG. 5 is a perspective view of the peristaltic pump and valve of the IOL of FIG. 4.

FIG. 5 shows that the exemplary peristaltic pump 56 has a tubular structure 56a formed of a flexible material that allows substantially conforming the shape of the tubular structure 56a to the shape of the channel 54. The pump 56 has two openings 56b and 56c that allow the entry and/or the exit of an optical fluid into and/or out of the tubular structure 56a. A valve 58, in the form of a slit, regulates the flow of the optical fluid through the tubular structure 56a, and thereby regulates the transfer of the optical fluid between the reservoir 46 and the chamber (FIG. 4). Similar to the slit 30a of the previous embodiment, the leakage of the optical fluid through the valve 58 in the absence of a pumping action is minimal.

The tubular structure 56a can be formed, for example, of silicone rubber, hydrogel or viscoelastic acrylic-copolymers, typically employed in construction of intraocular lenses, having a plurality of magnetic particles distributed therein. The magnetic particles can be selected, for example, to be ferrite, magnetite, nickel cobalt or compounds or alloys of such materials.

Figure 6A:
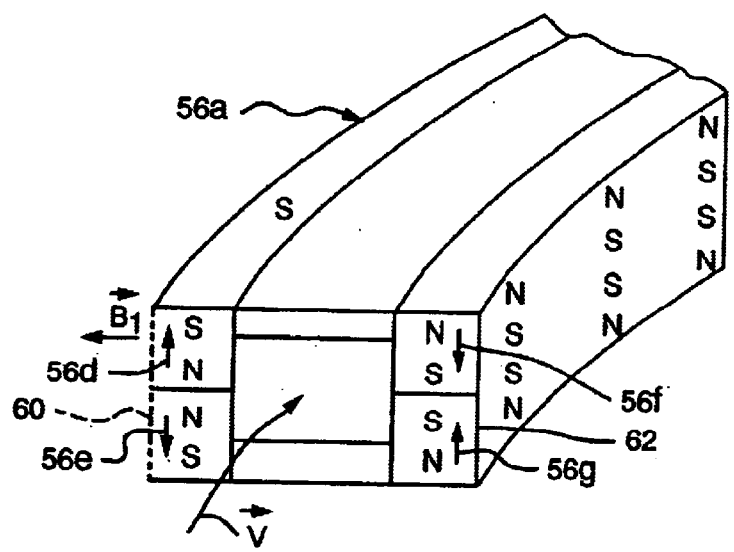
FIG. 6A is a fragmentary perspective view of a tubular structure forming the exemplary peristaltic pump of FIG. 5 schematically illustrating a plurality of magnetic particles distributed within two walls of the tubular structure.
Figure 6B:
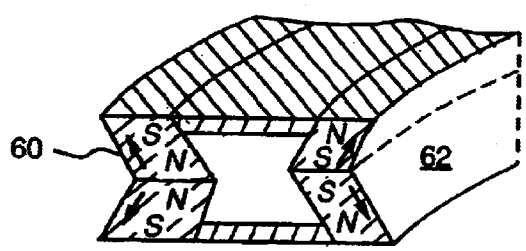
FIG. 6B illustrates a localized deflection induced in the walls of the peristaltic pump of FIG. 6A in response to an applied magnetic field, FIG. 6C schematically illustrates a propagating localized constriction induced in the peristaltic pump by an applied rotating magnetic field to force an optical fluid therethrough.
Figure 6C:
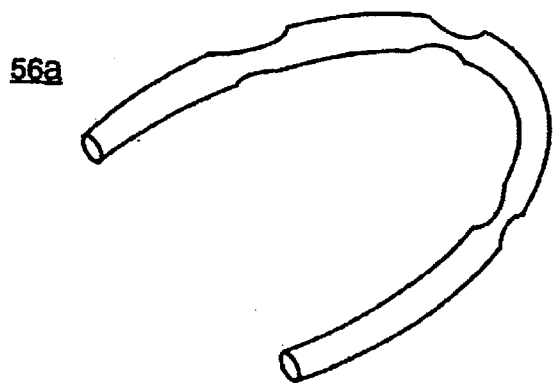

For example, FIG. 6A, a fragmentary perspective view of the tubular structure 56a, shows a plurality of magnetic moments, such as moments 56d, 56e, 56f, and 56g, and each having a north pole (N) and a south pole (S), which schematically depict an exemplary distribution of a plurality of magnetic particles within two walls 60 and 62 of the tubular structure 56a. A rotating magnetic field, such as a magnetic field $B_1$, can be applied to the tubular structure 56a, in a manner described below, to cause a propagating localized constriction in the structure 56a, thereby causing the flow of the optical fluid therethrough. For example, the magnetic field $B_1$, supplied by an external source and selected to be perpendicular to the moments 56d–56g and also perpendicular to a vector V directed along the channel formed by the walls of the tubular structure 56a, applies a torque to the moments 56d–56g to cause their localized deflection, and consequently the localized deflection of a portion of the tubular structure 56a, as shown in FIG. 6B. This deflection produces a localized constriction in the structure 56a. A rotation of the magnetic field $B_1$ in a plane parallel to a surface S of the tubular structure 56a causes the induced localized constriction to propagate along the structure 56a, as shown schematically in FIG. 6C. This propagating constriction forces the optical fluid to flow through the tubular structure 56a, and thereby to be transferred between a reservoir and an optical chamber of the IOL.

Figure 7A:
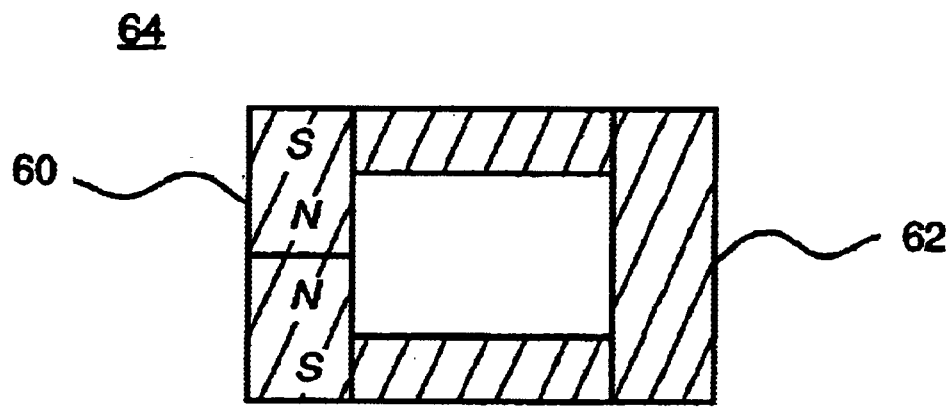
FIG. 7A is a cross-sectional view of another embodiment of the peristaltic pump of FIG. 5 illustrating a non-symmetric distribution of magnetic particles within the walls of the tubular structure of the pump.
Figure 7B:
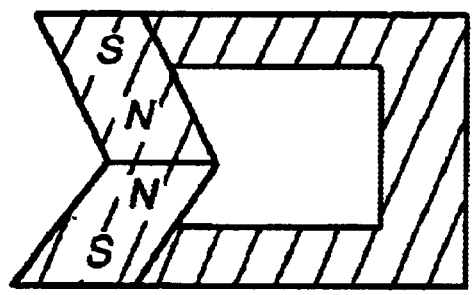
FIG. 7B illustrates a localized constriction formed in the peristaltic pump of FIG. 7A in response to an applied magnetic field.

Those skilled in the art will appreciate that distributions of magnetic particles other than those described above can be utilized to form a peristaltic pump according to the teachings of the invention. For example, the magnetic particles can be distributed within only one wall 60 of the tubular structure 56a, as shown schematically in FIG. 7A, to produce a non-symmetric tubular pump structure 64. The operation of the pump 64 is similar to that described above. In particular, a rotating magnetic field can be applied to cause a propagating constriction, such as the constriction shown in FIG. 7B, thereby causing a flow of the fluid through the pump.

One technique for manufacturing the micro-peristaltic pump 56 forms the walls of the pump through injection molding or casting as a one-piece or a two-piece wall structure. The material utilized for forming the wall structure can be, for example, a mixture of rubbery polymer resin and a fine powder of particles capable of being permanently magnetized. The particles are mixed with the resin in a non-magnetized state to improve the homogeneity of the distribution of the particles within the resin. The concentration of the particles can be, for example, up to approximately 50% of the volume of the mixture. The walls of the structure are then properly aligned and are exposed to a strong magnetic field, e.g., 1–4 Tesla, to properly orient the magnetization vectors of the particles. Subsequently, the resin is cured and the structure is removed from the dye. The wall structure can then be assembled, for example, into the optical body, glued at the appropriate locations and sealed to form the peristaltic pump 56.

FIG. 8 is an exploded perspective view of an intraocular lens device 66 according to another embodiment of the invention which employs diaphragm pumps 68 and 70 for pumping an optical fluid between a reservoir and an optical chamber of the lens. Similar to the previous embodiments, the lens 66 includes a cover portion 72 having a flexible optical membrane 72a, and further includes a base portion 74 having a reservoir 76 for storing an optical fluid. The IOL 66 also includes seats 78a and 78b for accommodating the diaphragm pumps 68 and 70, respectively. Further, valves 78c and 78d regulate the flow of the fluid between the reservoir 76 and the optical chamber of the IOL.

Figure 8A:
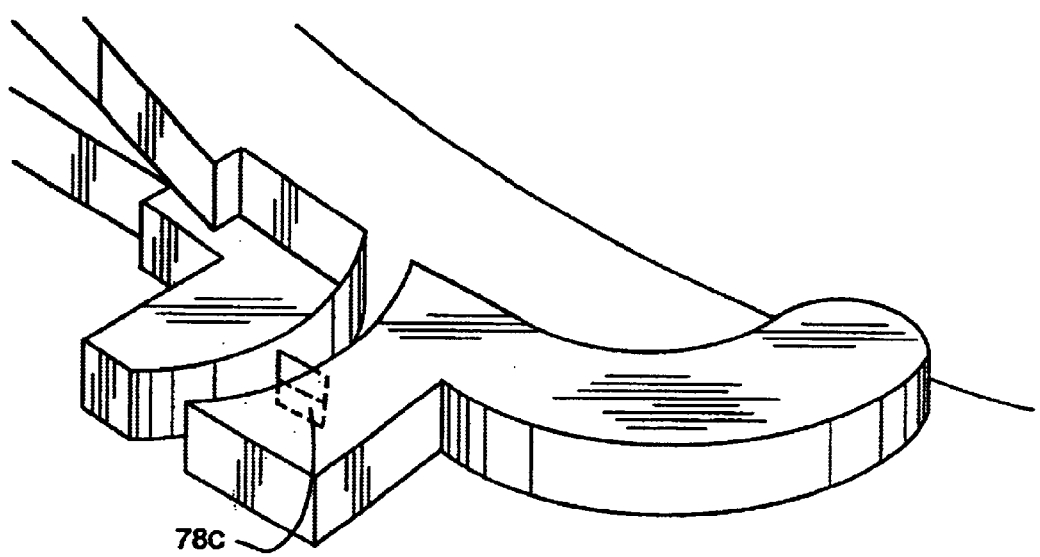
FIG. 8A is a fragmentary perspective view of a portion of the IOL of the previous FIG. 8, illustrating a valve for regulating fluid flow between the reservoir and the optical chamber.

FIG. 8A, which is a fragmentary view of a portion of the IOL 66, better illustrates one valve 78c. In particular, FIG. 8A illustrates that the valve 78c is in the form of a slit manufactured, for example, through ultra-sharp dissection of a barrier.

With reference to FIG. 9, each of the exemplary diaphragm pumps 68, 70 for use in the intraocular lens 66 can include a pump housing portion 80 having two openings 80a and 80b through which the optical fluid can flow into and/or out of the pump housing 80. A diaphragm lid 82 covers the housing portion 80. In one preferred embodiment of the invention, the lid 82 is magnetic, and hence can be mechanically modulated by applying an oscillatory magnetic field thereto. For example, attachment of a permanent magnet to a lid formed of silica can produce such a magnetic diaphragm lid. A magnetic field $B_2$, directed perpendicular to the magnetic diaphragm lid 82 and having an oscillatory magnitude, mechanically modulates the diaphragm lid 82, thereby causing fluid to be drawn in through a nozzle valve at opening 80a and expelled through another nozzle valve at opening 80b. Directional valves (not shown) located at openings 80a and 80b can insure a selected direction of flow when the pump is actuated.

The micro-fluidic components of the diaphragm pumps 68,70 can be fabricated, for example, by utilizing poly(dimethyl siloxane) (PDMS). A number of techniques can be employed for fabricating the micro-fluidic components. For example, an article entitled "Rapid prototyping of microfluidic switches in poly(dimethyl siloxane) and their actuation by electro-osmotic flow", published in J. Micromech. Mircoreng. 9 (1999) 211–217, and herein incorporated by reference, describes a methodology for fabricating mircofluidic components in PDMS.

Referring back to FIG. 8, a pumping action of one diaphragm pump, actuated, for example, by an external magnetic source, results in a transfer of a selected volume of an optical fluid between the reservoir 76 and an optical chamber formed between the cover portion 72 and the base portion 74. Selectively activating one of the diaphragm pumps provides a flow of fluid into or out of the optical chamber.

Another preferred embodiment of the invention employs a micro-pump that utilizes a ferro-fluid material, such as ferrofluids based on $Fe_3O_4$, Co, Fe or $Fe_3N$ nano-particles, to provide a pumping action for transferring an optical fluid between a reservoir and an optical chamber of an intraocular lens of the invention.

FIG. 10 is an exploded view of an intraocular lens 84 according to such an embodiment. The IOL 84 includes a cover portion 86 having a flexible membrane 86a, and a base portion 88 having a reservoir 88a, a channel 88b for providing fluid communication between the reservoir 88a and a chamber that is formed between the cover portion 86 and the housing portion 88. A valve 88c regulates the fluid communication between the reservoir 88a and the optical chamber.

Figure 11:
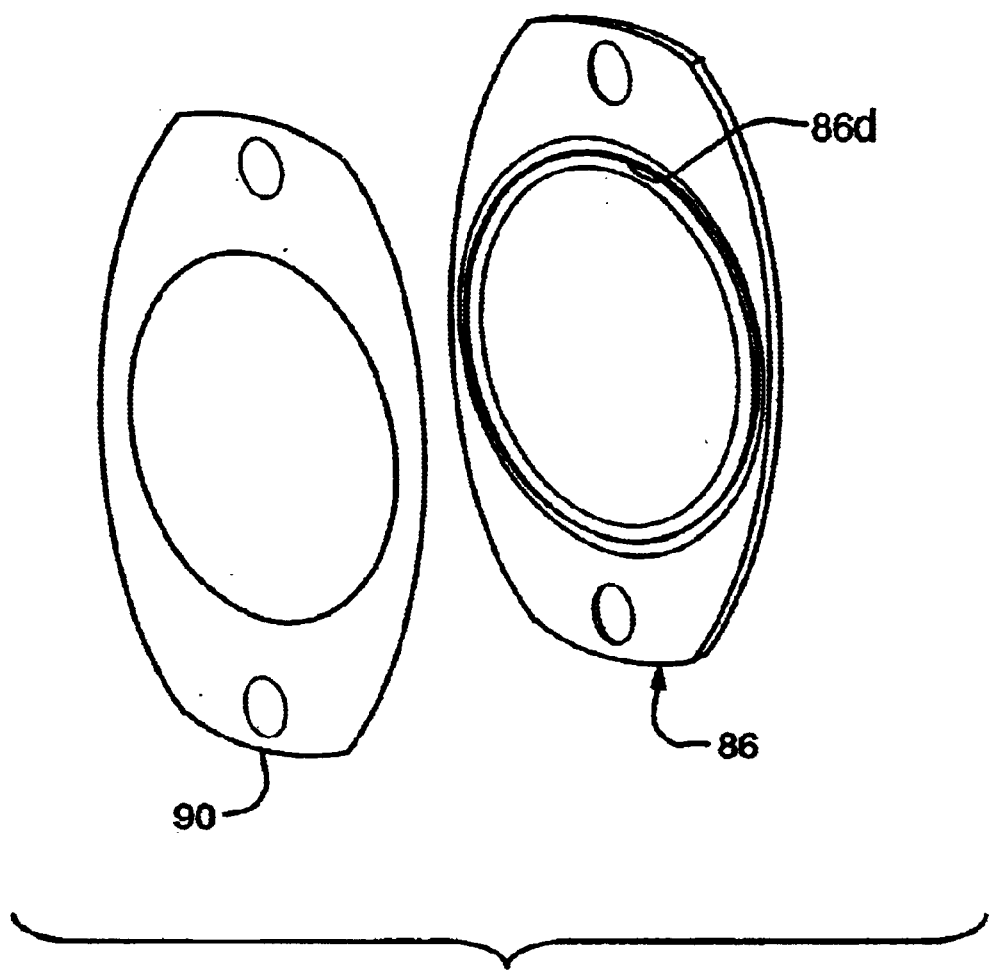
FIG. 11 is a perspective view of the cover portion and the flexible membrane (barrier film) separating the cover portion from the base portion of the IOL of FIG. 10, where the cover portion includes a channel for storing a selected volume of a ferrofluid material.

FIG. 11 illustrates that the cover portion includes a channel 86d in which a selected volume of a ferro-fluid material is stored. With reference to both FIGS. 10 and 11, a flexible barrier film 90 separates the cover portion 86 from the base portion 88, thereby isolating the ferro-fluid from the optical fluid.

Figure 12:
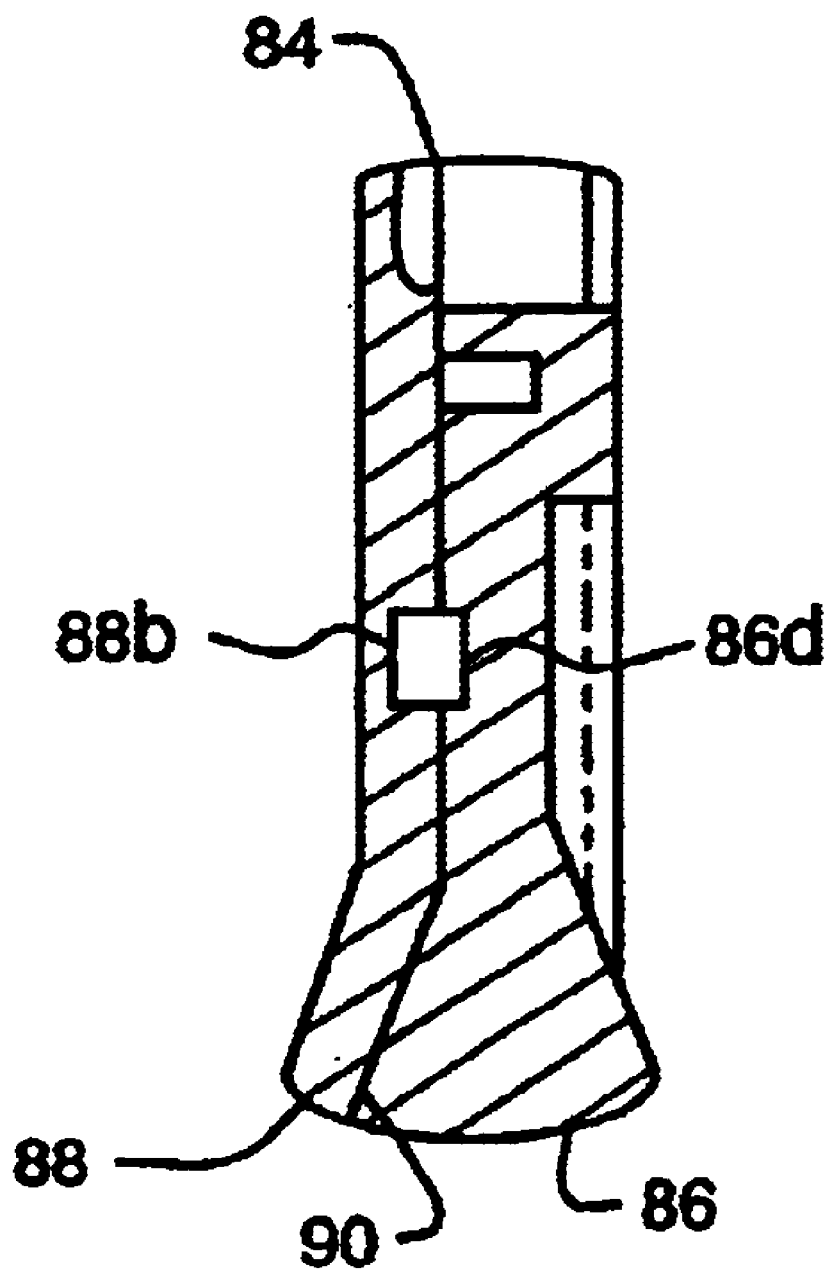
FIG. 12 is a partial cross-sectional view of the IOL of FIGS. 10 and 11 illustrating the juxtaposition of the channel for storing the ferro-fluid material relative to the channel providing a flow path for an optical fluid between the reservoir and the optical chamber of the IOL.

FIG. 12, a partial cross-sectional view of the IOL 84, illustrates the uxtaposition of the channel 86d, utilized for storing the ferro-fluid, relative to the channel 88b that provides a flow path for the optical fluid. The channel 86d is substantially aligned relative to the channel 88b, and is separated therefrom by the flexible membrane 90.

Figure 13:
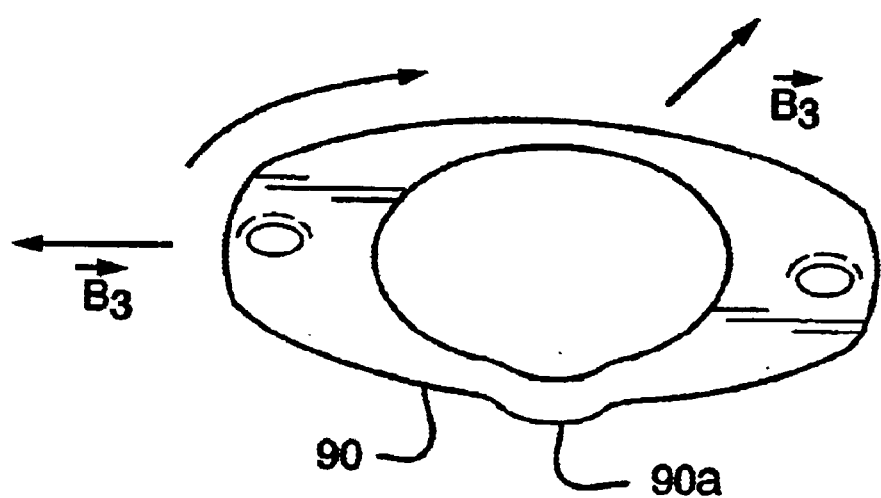
FIG. 13 is a perspective view of the membrane (barrier film) separating the cover portion and the base portion of the IOL of FIG. 10, schematically illustrating a localized propagating deflection induced in the membrane by a ferro-fluid subjected to an external magnetic field.

Referring to FIGS. 10, 11, 12, and 13, the application of an exemplary magnetic field $B_3$, supplied by an external source (not shown), and rotating in a plane parallel to the plane of the membrane 90, to the ferro-fluid can cause a motion of the ferro-fluid through the channel 86d. Such a motion of the ferro-fluid causes localized deflections, such as a deflection 90a, of the membrane 90 separating the channel 86d from the channel 88b (FIGS. 12 and 13). The rotation of the magnetic field causes the local deflection in the membrane 90 to propagate around the membrane over the channel 88b, thereby forcing the flow of the optical fluid through the channel 88b between the reservoir 88a and the optical chamber. A reversal of the rotational direction of the magnetic field causes the flow of the optically fluid in a reverse direction. Thus, the optical fluid can be pumped into or out of the optical chamber by simply selecting the sehse of rotation of the magnetic field $B_3$.

In some embodiments of the invention, the direction of the magnetic field $B_3$ is selected such that it has a component perpendicular to the membrane 90 and a component in the direction of the channel 86d. The perpendicular component advantageously presses the ferro-fluid material against the membrane 90, thereby accentuating a deflection formed in the membrane 90. The membrane 90 can be formed, for example, of elastic polymers, such as silicone rubber. Further, the membrane 90 can be surface coated in a manner known in the art to inhibit diffusion of fluid therethrough.

Figure 14:
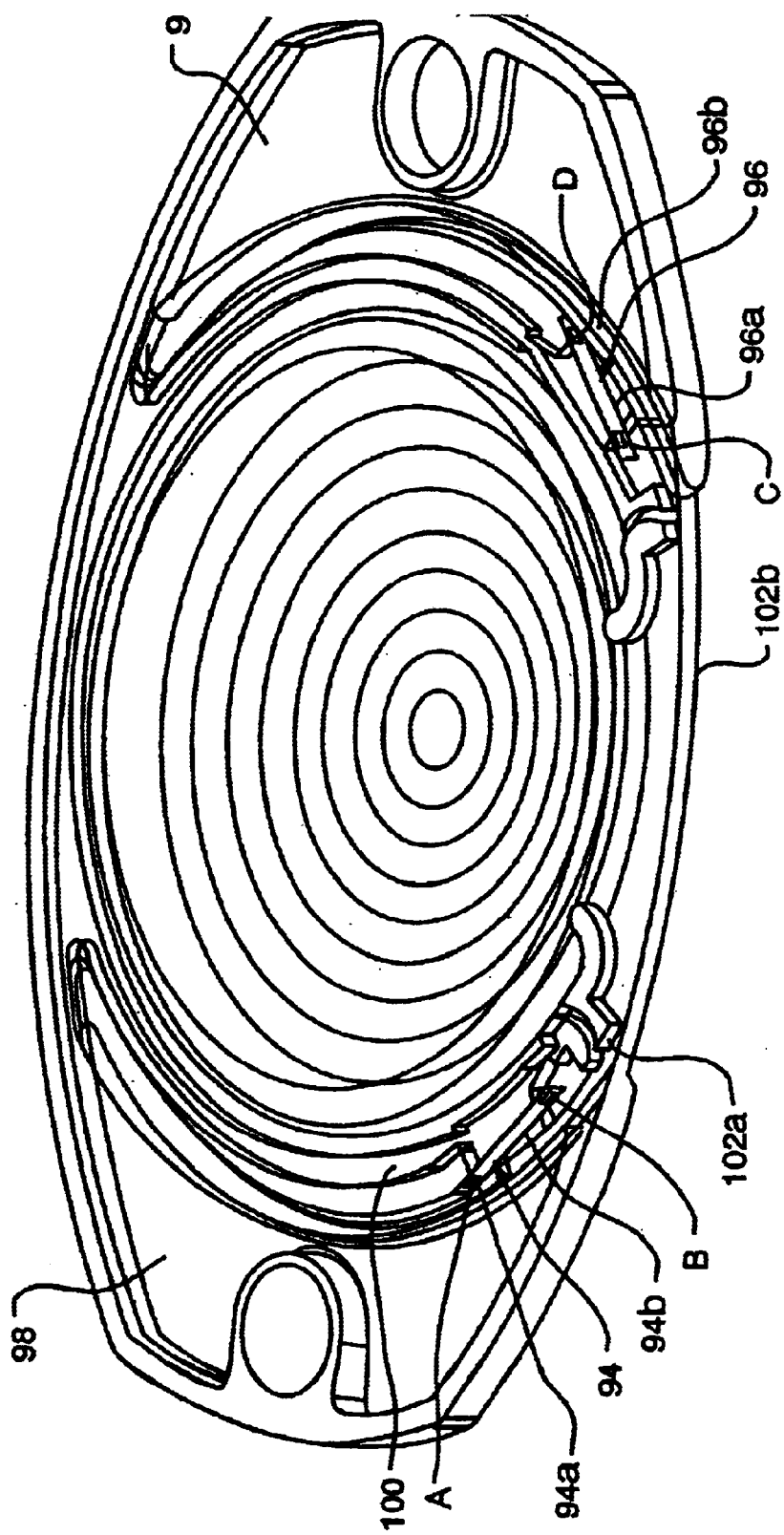
FIG. 14 is a perspective view of the base portion of an IOL according to another embodiment of the invention which employs micro-pumps formed of a pair of permanent magnets to pump an optical fluid between a reservoir and an optical chamber.

FIG. 14 illustrates a base portion 92 of an intraocular lens according to another preferred embodiment of the invention which includes a pair of magnetic micropumps 94 and 96. Similar to the previous embodiments, the base portion 92 includes a reservoir 98 for storing an optical fluid (not shown), and a channel 100 for providing fluid communication between the reservoir 98 and an optical chamber (not shown), such as the optical chamber 18 shown in FIGS. 1A and 1B. Each micro-pump 94 and 96 includes two permanent magnets 94a,b and 96a,b, pivoted about points A, B, and C, D, respectively. A pair of valves 102a,b regulate transfer of the optical fluid between the reservoir 98 and the channel 100.

Figure 15A:
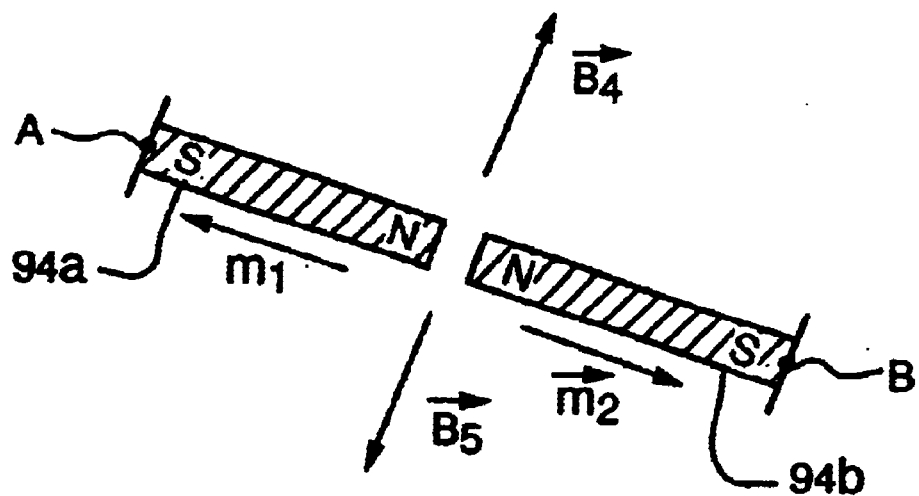
FIG. 15A is a partial top view of the permanent magnets forming one of the pair of micro-pumps of FIG. 14.
Figure 15B:
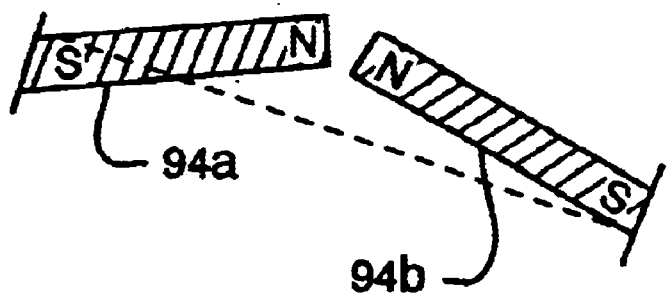
FIG. 15B illustrates a deflection of the magnets of FIG. 15A in response to an externally applied magnetic field.

The operation of the micro-pumps 94 and 96 can be understood by reference to FIGS. 15A and 15B which show that the permanent magnets 94a,b of the micro-pump 94, for example, are situated such that a North pole (N) of the magnet 94a faces a North pole (N) of the magnet 94b. The magnets 94a and 94b can be characterized as magnetic moments $m_1$ and $m_2$, each with a direction extending from the North pole (N) of the magnet to its South pole (S). Application of a magnetic field, such as a magnetic field $B_4$ supplied by an external magnetic source, lying in the plane of the base portion 92 (FIG. 14) and preferably selected to be perpendicular to the directions of the magnetic moments $m_1$ and $m_2$ causes a deflection of the magnets 94a and 94b, as shown in FIG. 15B. A reversal of the direction of the magnetic field $B_4$, i.e., application of a magnetic field $B_5$, results in a deflection of the magnets 94a and 94b in an opposite direction. Hence, an oscillating field whose direction switches between those of the magnetic fields $B_4$ and $B_5$ results in a mechanical oscillation of the magnets 94a and 94b. Such a mechanical oscillation forces an optical fluid (not shown) to be transferred between the reservoir 98 and channel 100. The micro-pump 96 also operates in a similar fashion.

FIG. 16 is an exploded view of yet another embodiment of an intra-ocular lens 104 according to the teachings of the present invention which includes a cover portion 106, a base portion 108, and a retaining film 110. The cover portion 106 includes a channel 112 for seating a ball 114 formed of soft magnetic material. The retaining film 110, the cover portion 106, and the housing portion 108 are preferably formed of a resilient material such as silicone. In particular, a bottom surface 112a of the channel 112 is formed of a material, such as silicone, that is sufficiently resilient to deform under the magnetic forces of the ball 114. Similar to the previous embodiments, the base portion 108 includes a reservoir 108a for storing an optical fluid (not shown), a membrane or integral lens portion 116 (preferably selected to be deformable), and a channel 118 which is substantially aligned with the channel 112. The channel 118 provides fluid communication between the reservoir 108a and a chamber that is formed between the cover portion 106 and the base portion 108 upon connecting them together.

A rotating external magnetic field having a large gradient can be applied to the ball 114 from a direction below the base portion 108 to cause it to press against the surface 112a of the channel 112, thereby accentuating a local deflection of the surface 112a in the vicinity of the ball 114. The magnetic field can also be selected to have a component to cause the ball to move along the channel 112. As the deflection in the surface 112a of the channel 112 propagates with the motion of the ball around the channel 112, it forces the optical fluid to flow in the channel 118 of the base portion 108 between the reservoir 108a and the optical chamber. Thus, the ball 114 functions as a peristaltic pump to pump the optical fluid into or out of the optical chamber, thereby changing the hydrostatic pressure on the membrane 114 and 116. The change in the hydrodstatic pressure within the optical chamber causes a selected deflection of the flexible membranes 114 and 116, thereby causing a change in the focusing performance of the lens.

Figure 17:
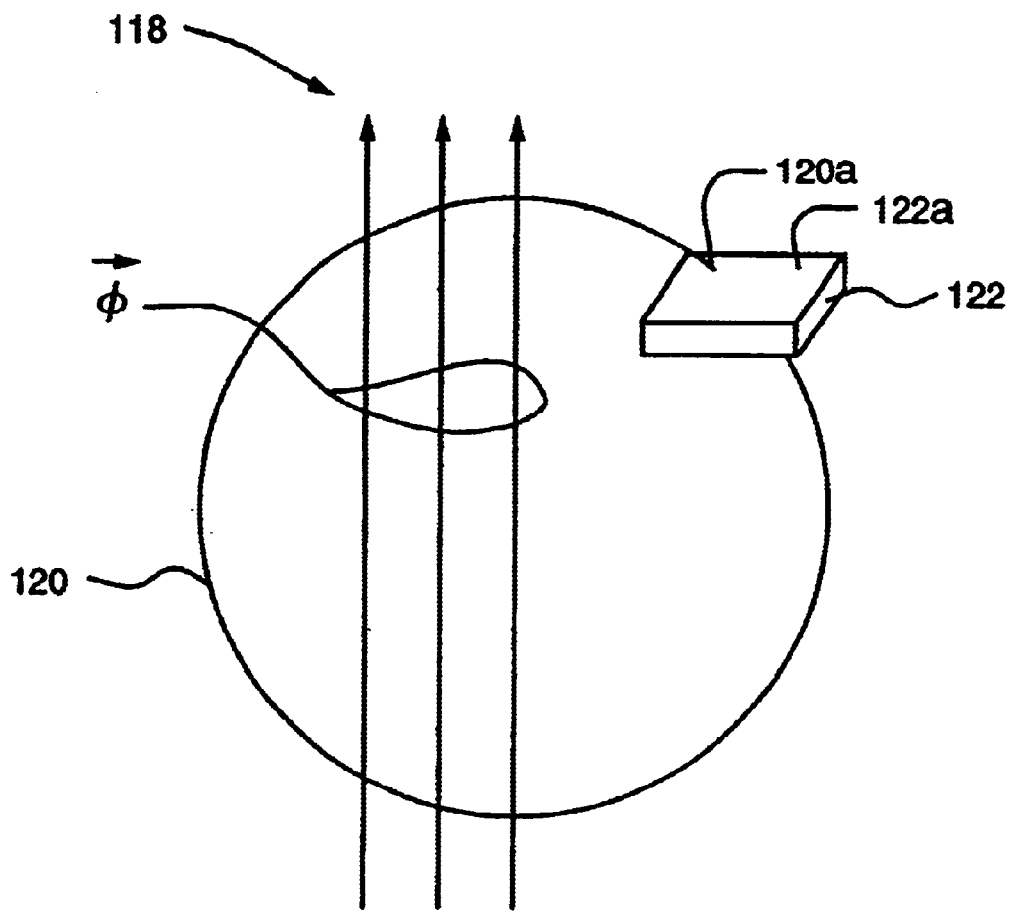
FIG. 17 is a perspective view of a micro-pump according to the teachings of the invention which employs a piezo-electric element for driving a diaphragm pump.

Another preferred embodiment of the invention employs a micro-pump 118, shown in FIG. 17, that utilizes a piezo-electric actuating element 120 to drive a diaphragm 122a of a diaphragm pump 122, similar to the diaphragm pump 68 of FIG. 8. Application of a time-varying magnetic flux $\phi$ o the area partially enclosed by the exemplary semi-circular actuating element 120, induces a voltage differential between the ends 120a and 120b of the element 120 through Faraday effect. Because the actuating coil element 120 is formed of a piezo-electric active material, the induced voltage differential causes a change in the stress within the piezoelectric material, which in turn causes a mechanical movement of the diaphragm 122a. A modulation of the rate of the time variation of the flux $\phi$ results in a modulation of the stress in the element 120, which in turn causes a mechanical oscillation of the diaphragm 122a. This mechanical oscillation of the diaphragm 122a, as described in connection with the embodiment of FIGS. 8 and 9, results in a pumping action that transfers the optical fluid between the reservoir and the optical chamber of an intraocular lens of the invention.

A material employed for forming the actuating element 120 is selected to exhibit a change of length sufficient for driving the diaphragm of the pump 122 in response to a voltage differential induced across it which is safe for the individual in whose eye the lens is implanted. For example, materials, known as electroactive polymers (EAP), can be utilized to form the actuating element 120. Such materials typically exhibit large displacements in response to relatively modest applied electric fields.

One advantage of the micro-pump 118 is that it does not employ any magnetic components which may interfere with diagnostics equipment, such as magnetic resonance imaging (MRI) machines which employ very high magnetic fields.

Figure 18:
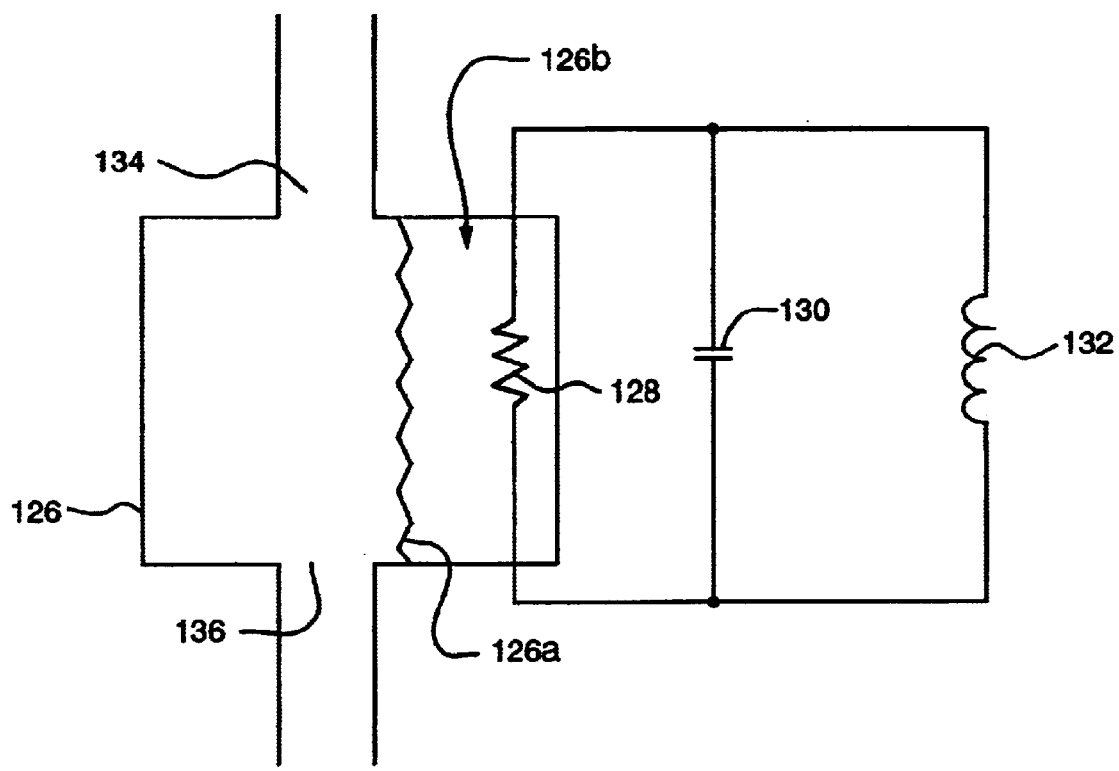
FIG. 18 is a schematic diagram of a vapor-driven pump according to the teachings of the present invention.

Another embodiment of an intra-ocular lens of the invention employs a vapordriven micro-pump 124, as shown in FIG. 18 for causing a flow of an optical fluid between a reservoir and an inner chamber (not shown). The vapor-driven pump 124 includes a housing 126 having a flexible diaphragm 126a that separates a reservoir 126b from the remainder of the interior of the housing 126. A selected volume of a fluid, such as water, is stored in the reservoir 126b. A resistive element 128, that can preferably form a resonant circuit with a capacitor 130 and an inductor 132, can be utilized to periodically heat up the fluid within the reservoir to turn it into vapor. This exerts a periodic pressure on the membrane 126a and hence causes a periodic deflection, i.e., oscillation, thereof. For example, an external magnetic source can be employed to provide a time-varying flux, preferably having a frequency close to the resonant frequency of the circuit, through the inductor 132, thereby energizing the resonant circuit. The oscillation of the flexible membrane 126a can in turn cause a flow of a fluid from an input port, such as a port 134, having a nozzle valve (not shown) through the interior of the housing 126 to an exit port, such as a port 136, having a nozzle valve (not shown).

Figure 19:
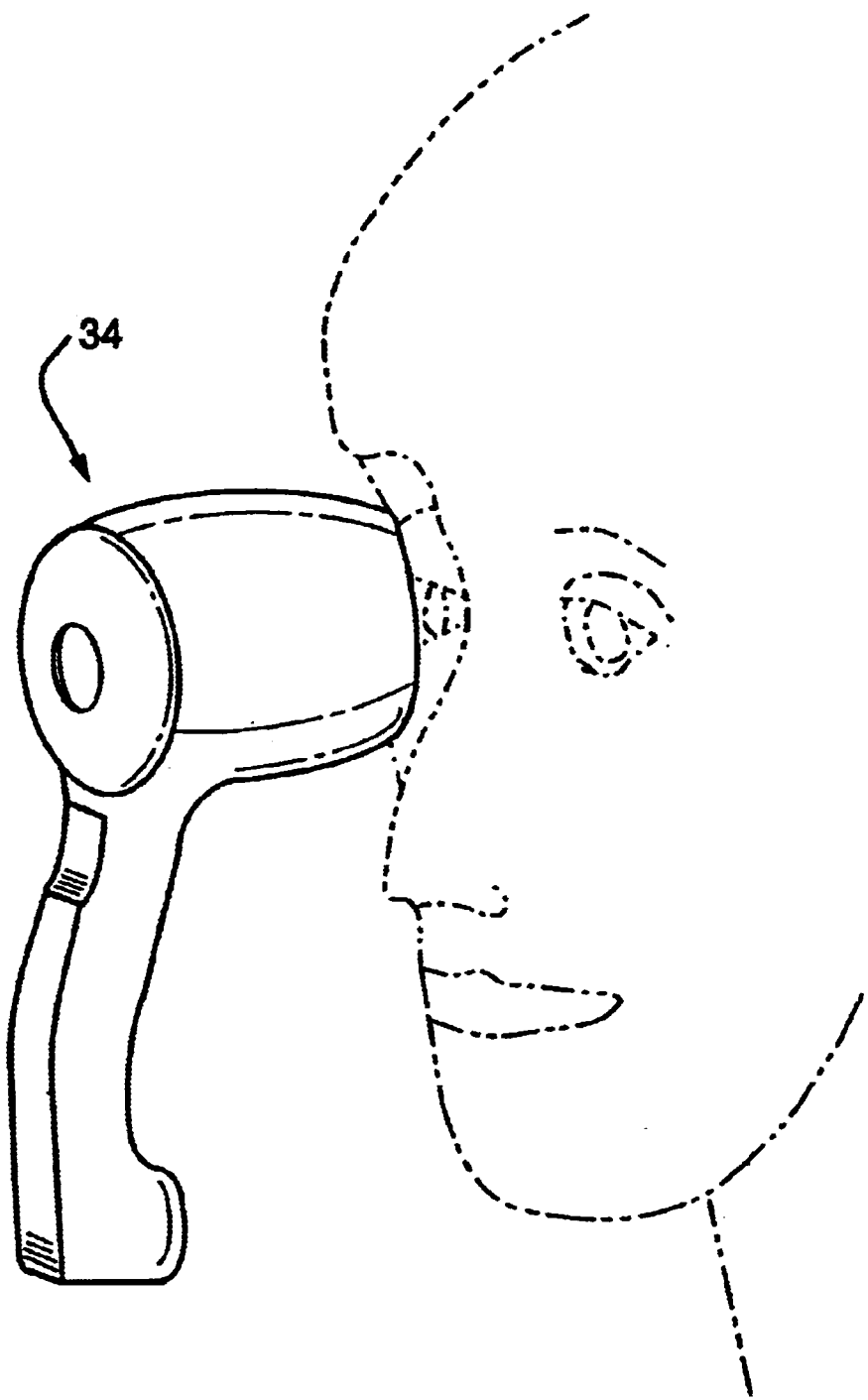
FIG. 19 is a perspective view of a device for externally adjusting the focusing performance of an IOL device of the invention.

As discussed above, an external energy source, such as an electric or a magnetic source, can be employed to externally adjust the focusing performance of an intraocular lens of the invention. FIG. 19 illustrates a device 134 for externally adjusting the focusing performance of an intra-ocular lens of the invention that has been implanted in a patient's eye. The device 134 can include an energy source, and can further include calibration mechanism for adjusting the focusing performance of the lens by a pre-defined value.

Figure 20:
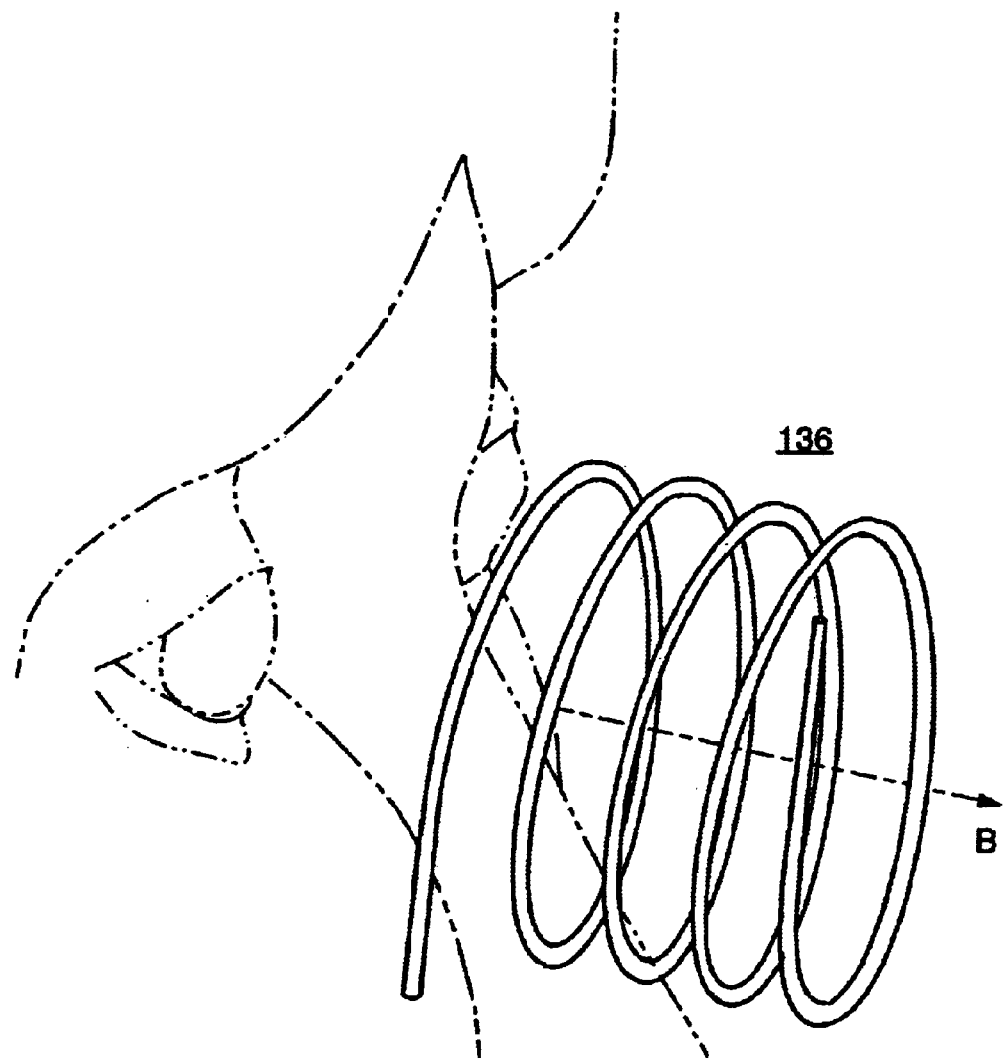
FIG. 20 is a perspective view of a magnetic field generator (e.g., coil) that can be utilized as an external energy source for adjusting the focusing performance of an IOL lens of the invention.

A number of different energy sources can be utilized in the device 134 for actuating a micro-pump of an IOL of the invention. For example, FIG. 20 illustrates magnetic field generator 136 in the form of a coil through which a current can flow to produce a magnetic field, e.g., a field B, along an axial direction thereof. A change in the magnitude of the current flowing through the coil can cause a change in the strength of the magnetic field, and a change in the direction of the current flow can cause a change in the direction of the field. In a preferred embodiment, the coil 136 forms a resonant circuit with an inductor and a capacitor to produce an oscillating magnetic field having a predefined frequency, for example, a frequency that is substantially similar to mechanical vibrational frequency of the diaphragm of the diaphragm pump of FIG. 9. Such a magnetic field generator can be employed, for example, to tune the focusing performance of the embodiment of the intraocular lens of the invention shown in FIG. 8 or 17.

Figure 21:
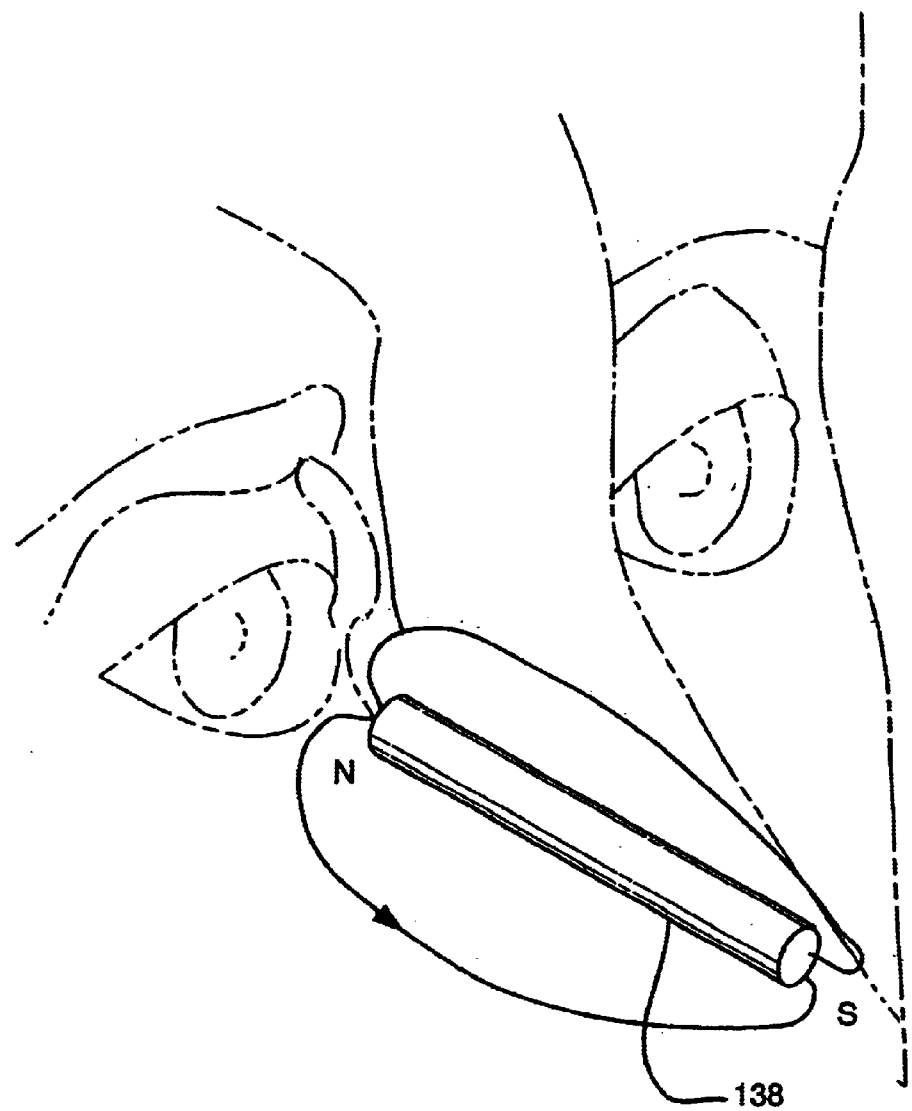
FIG. 21 is a perspective view of another magnetic field generator that can be utilized as an external energy source for adjusting the focusing performance of an IOL lens of the invention.

FIG. 21 illustrates another magnetic field generator 138 that can be utilized to externally adjust the refractive power of an intraocular lens of the present invention. The magnetic field generator 138 includes a magnet having a North pole ("N") and a South pole ("S"). Magnetic field lines 138a emanate from the North pole and terminate at the South pole. The field generator 138 can be positioned in the proximity of a patient's eye having an IOL of the invention such that at least some of the magnetic field lines 138a penetrate the eye. A rotation of the field generator external of the eye can then cause, for example, a rotating magnetic field that can be utilized in a number of embodiments of the invention, such as the embodiment having a peristaltic micro-pump.

Figure 22:
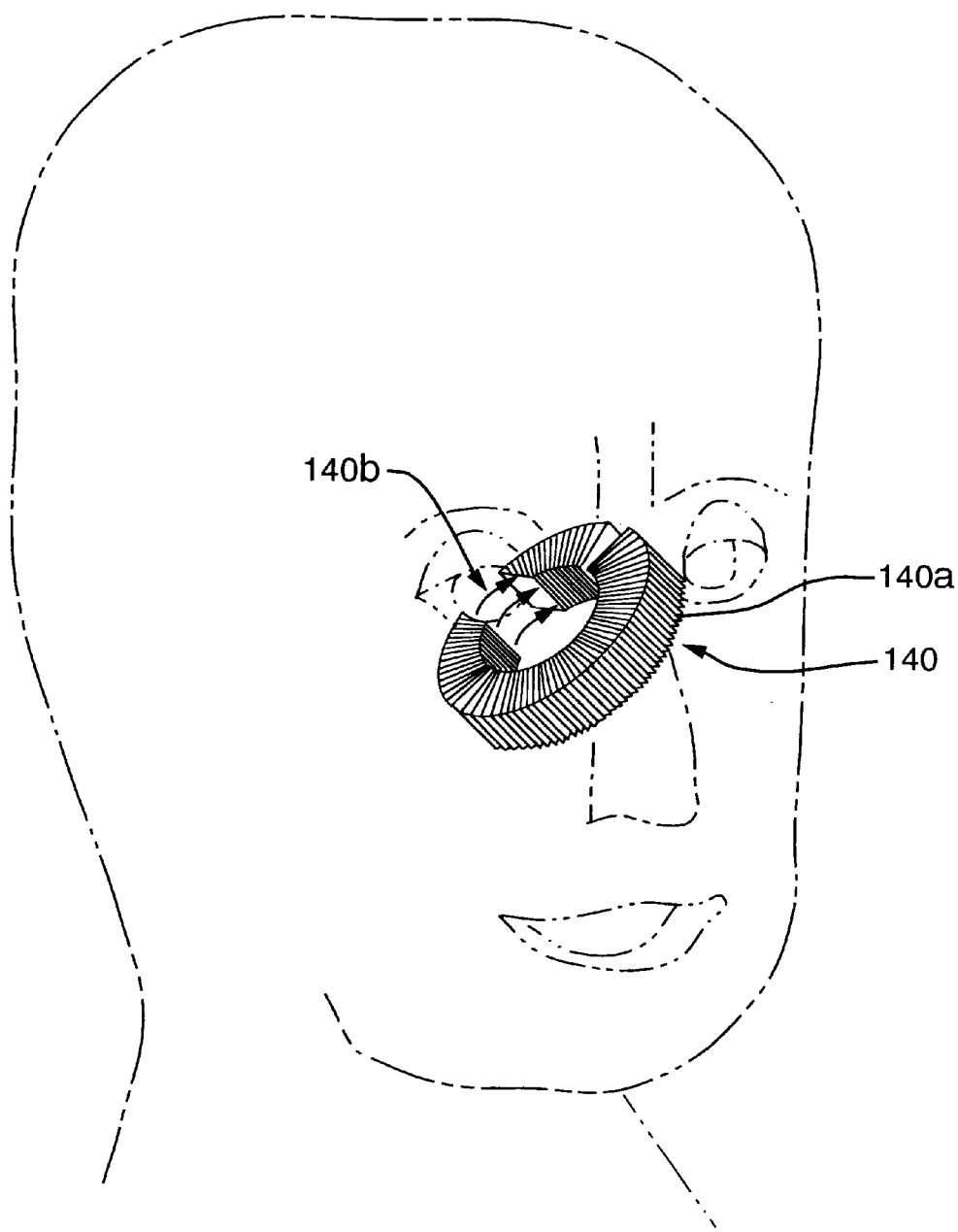
FIG. 22 is a perspective view of another magnetic field generator having an electromagnet for use in externally adjusting the focusing performance of the lens of the invention.

FIG. 22 illustrates another magnetic field generator 140 that can be utilized in various embodiments of the present invention for adjusting the focusing performance of the IOL. The magnetic field generator 140 includes an electromagnet 140a for generating a magnetic field, such as a field represented by field lines 140b. A reversal of a current through the electromagnet results a reversal of the direction of the magnetic field. Further, the strength of the magnetic field can be changed by increasing or decreasing the current flowing through the electromagnet. Such a magnetic field generator can be employed as an external energy source, for example, in the embodiments of the invention having a gear pump or a peristaltic pump, or a piezoelectric driven pump.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. An intraocular lens, comprising
   an optical chamber for receiving an optical fluid and having at least a flexible region deformable under influence of a fluid,
   a refractive optical fluid having an index of refraction greater than about 1.337,
   a reservoir for storing an optical fluid and being in fluid communication with said chamber,
   a valve for regulating the fluid communication between said optical chamber and said reservoir.

2. The IOL of claim 1, further comprising a pump capable of being actuated by an energy source positioned external of the eye for pumping the optical fluid between said reservoir and said optical chamber to modify a volume of said refractive fluid within said optical chamber to adjust a focusing performance of said lens.

3. The IOL of claim 2, wherein said pump causes flow of a selected volume of the optical fluid between said reservoir and said optical chamber after said lens is implanted in the eye to selectively vary an amount of the fluid in the optical chamber, thereby selectively varying the focusing performance of said lens.

4. The IOL of claim 2, further comprising at least one lens movable in response to movement of the fluid to vary focusing performance of the IOL.

5. The IOL of claim 2, wherein said source produces a magnetic field for actuating said pump.

6. The IOL of claim 5, wherein said magnetic field is oscillatory.

7. The IOL of claim 5, wherein said magnetic field is a rotating field.

8. The IOL of claim 2, wherein said pump is a peristaltic pump.

9. The IOL of claim 8, wherein said peristaltic pump has a tubular structure.

10. The IOL of claim 9, wherein said tubular structure is formed of an elastic material having magnetic particles therein.

11. The IOL of claim 10, wherein said magnetic particles are distributed within said elastic material such that a rotating magnetic field applied to said tubular structure induces a propagating deformation in said structure.

12. The IOL of claim 11, wherein said magnetic particles are selected from the group consisting of Samarium, Neodymium, Cobalt, Iron, Nickel, Boron, ferrite, magnetic, and nickel cobalt.

13. The IOL of claim 9, wherein a slit within said tubular structure forms said valve.

14. The IOL of claim 2, wherein said pump includes a gear pump.

15. The IOL of claim 14, wherein said gear pump includes two inter-locking gears.

16. The IOL of claim 15, wherein one of said gears is magnetic.

17. The IOL of claim 16, wherein said external energy source applies a rotating magnetic field to said magnetic gear to cause rotations of said inter-locking gears, thereby causing transfer of the fluid between said optical chamber and said reservoir.

18. The IOL of claim 14, wherein said gear pump is formed of silicone rubber and further comprises a magnetic gear with a permanent magnet.

19. The IOL of claim 2, wherein said pump is a diaphragm pump.

20. The IOL of claim 19, wherein said diaphragm pump is configured to be magnetically actuated.

21. The IOL of claim 19, wherein said diaphragm pump is configured to be electrically actuated.

22. The IOL of claim 19, wherein said diaphragm pump includes a housing having an inlet opening and an outlet opening, and a flexible diaphragm disposed to be in mechanical communication with said housing.

23. The IOL of claim 22, wherein said flexible diaphragm is configured to have at least one resonant vibrational frequency.

24. The IOL of claim 22, wherein said flexible diaphragm is magnetic.

25. The IOL of claim 24, wherein said external source applies an oscillatory magnetic field to said flexible diaphragm to cause a mechanical oscillation thereof, thereby actuating said pump.

26. The IOL of claim 25, wherein said oscillatory magnetic field has an oscillation frequency substantially similar to said resonant vibrational frequency of said flexible diaphragm to induce a large amplitude oscillation of said flexible diaphragm, thereby causing a flow of the optical fluid through the housing of the pump between the inlet opening and the outlet opening.

27. The IOL of claim 2, wherein said pump is a ferro-fluid pump.

28. The IOL of claim 27, wherein said IOL includes a base portion having said reservoir and having a first channel for providing fluid communication between said reservoir and said optical chamber, said IOL further including a cover portion having a second channel for storing a ferro-fluid material, said first and second channels being substantially aligned.

29. The IOL of claim 28, further comprising a flexible membrane disposed between said first and second channels to isolate said ferro-fluid material from said optical fluid.

30. The IOL of claim 29, wherein said ferro-fluid material can be actuated by said external energy source to provide a propagating pressure on said flexible membrane to produce a propagating deformation of said membrane which causes transfer of said optical fluid between said reservoir and said chamber through said second channel.

31. The IOL of claim 29, wherein said ferro-fluid material is selected from the group consisting of nanoparticles of Magnetite ($Fe_3O_4$), Cobalt, Nickel, Iron Nitride and Iron.

32. The IOL of claim 29, wherein said flexible membrane is formed of silicone rubber.

33. The IOL of claim 2, wherein said pump includes at least a first magnet pivoted about a rotation axis at an end thereof and positioned between said reservoir and said optical chamber in a path of fluid flow, said magnet being actuated by a magnetic source external of the eye to rotate about said rotation axis, thereby causing flow of the fluid through said valve between said reservoir and said optical chamber.

34. The IOL of claim 33, further comprising a second magnet positioned along a vector directed from one pole of the first magnet to its other pole such that the opposite poles of the first and second magnets are proximate of each other, said first and second magnets being actuated by the external source to rotate in opposite directions, thereby causing a flow of the fluid through said valve between said reservoir and said optical chamber.

35. The IOL of claim 2, wherein said pump includes at least one ball formed of a soft magnetic material and being actuated by said external energy source.

36. The IOL of claim 35, wherein said IOL includes a base portion having said reservoir for storing an optical fluid and a cover portion having a channel for housing said at least one ball and having at least a flexible portion in proximity of at least a portion of the optical fluid.

37. The IOL of claim 36, wherein said external energy source actuates said at least one ball to move within said channel such that it produces a propagating deformation of said flexible portion which in turn causes flow of said fluid between the reservoir and the optical chamber.

38. The IOL of claim 37, further comprising a membrane positioned over the cover portion to maintain said ball in said channel.

39. The IOL of claim 2, wherein said pump is a piezo-electrically actuated diaphragm pump.

40. The IOL of claim 39, wherein said piezo-electrically actuated diaphragm pump includes
a housing having an inlet opening and an outlet opening,
a flexible membrane in mechanical communication with said housing, and
an elongated piezo-electric element in contact with said flexible membrane such that a time-varying magnetic flux produced by an energy source induces a current through said piezo-electric element to change the stress in said piezoelectric element, thereby mechanically moving said diaphragm.

41. The IOL of claim 40, wherein said energy source modulates the rate of change of said time-varying flux to modulate the stress in said piezo-electric element, thereby modulating said diaphragm.

42. The IOL of claim 1, wherein two optical surfaces joined at peripheries thereof form said optical chamber.

43. The IOL of claim 42, wherein at least one of said surfaces includes a diffractive pattern.

44. An intraocular lens, comprising,
an optical chamber having at least a flexible region deformable under influence of a fluid,
a reservoir for storing an optical fluid and being in fluid communication with said chamber,
a valve for regulating the fluid communication between said optical chamber and said reservoir, and
a vapor-operated pump capable of being actuated by an energy source positioned external to the eye.

45. The IOL of claim 44, wherein said vapor-operated pump includes a housing having a first portion for providing a passageway for the optical fluid between an input port and an output port, and having a second portion for storing a fluid, said housing having a flexible diaphragm separating said first portion from said second portion.

46. The IOL of claim 45, wherein said vapor-driven pump further includes a resonant resistive, inductive, and capacitive circuit adapted to periodically transfer energy to said fluid to periodically turn said fluid into vapor.

47. The IOL of claim 46, wherein said energy source emits oscillatory magnetic field having a frequency substantially similar to resonant frequency of said resonant circuit such that a flux of said magnetic field through an inductive element energizes said resonant circuit to transfer energy to said fluid.

48. A method for adjusting a focusing performance of an intraocular lens externally of the eye, comprising
providing an intraocular lens comprising
an optical chamber for receiving an optical fluid having at least a flexible region deformable under influence of a fluid,
a refractive optical fluid having an index of refraction greater than about 1.337,
a reservoir for storing an optical fluid and being in fluid communication with said chamber,
a valve for regulating the fluid communication between said optical chamber and said reservoir, and
a pump capable of being actuated by an external energy source;
actuating said pump by the external energy source to transfer a selected volume of the optical fluid between said reservoir and said optical chamber, thereby adjusting the focusing performance of the intraocular lens.

49. An intraocular lens, comprising
an optical chamber for receiving an optical fluid and having at least a flexible region deformable under influence of a fluid,
a refractive optical fluid having an index of refraction greater than 1.337,
a reservoir for storing an optical fluid and being in fluid communications with said chamber, a valve for regulating the fluid flow between said optical chamber and said reservoir, and a pump capable of being actuated by an energy source positioned external of the eye for pumping the optical fluid between said reservoir and said optical chamber to modify a volume of said refractive fluid within said optical chamber to adjust a focusing performance of said intraocular lens.

* * * * *